(12) United States Patent
Raghavan et al.

(10) Patent No.: US 10,231,704 B2
(45) Date of Patent: Mar. 19, 2019

(54) METHOD FOR ACQUIRING ULTRASONIC DATA

(71) Applicants: Raghu Raghavan, Baltimore, MD (US); Timothy Poston, Bangalore (IN)

(72) Inventors: Raghu Raghavan, Baltimore, MD (US); Timothy Poston, Bangalore (IN)

(*) Notice: Subject to any disclaimer, the term of this patent is extended or adjusted under 35 U.S.C. 154(b) by 991 days.

(21) Appl. No.: 14/568,138

(22) Filed: Dec. 12, 2014

(65) Prior Publication Data

US 2015/0173715 A1    Jun. 25, 2015

Related U.S. Application Data

(60) Provisional application No. 61/918,664, filed on Dec. 20, 2013, provisional application No. 62/040,007, filed on Aug. 21, 2014.

(51) Int. Cl.
*A61B 8/00* (2006.01)
*A61B 8/08* (2006.01)
(Continued)

(52) U.S. Cl.
CPC ............ *A61B 8/46* (2013.01); *A61B 8/4245* (2013.01); *A61B 8/4254* (2013.01); *A61B 8/52* (2013.01);
(Continued)

(58) Field of Classification Search
CPC ....... A61B 8/00; A61B 8/0866; A61B 8/4245; A61B 8/4254; A61B 8/4263; A61B 8/46;
(Continued)

(56) References Cited

U.S. PATENT DOCUMENTS 7,758,509 B2   7/2010  Angelsen et al.
8,348,846 B2   1/2013  Gunther et al.
(Continued)

OTHER PUBLICATIONS

Hsu et al., Freehand 3D Ultrasound Calibration: A Review, CUED/F-INFENG/TR 584, Dec. 2007, University of Cambridge Department of Engineering, pp. 1-30.
(Continued)

*Primary Examiner* — Carolyn Pehlke
(74) *Attorney, Agent, or Firm* — DLA Piper LLP (US)

(57) ABSTRACT

Methods for acquiring ultrasonic data are disclosed. An image-acquiring system is provided. A three-dimensional target region is selected. A plurality of fiducial positions corresponding to anatomical features in the target region are calculated. A model of the target region comprising a plurality of target locations representing a plurality of planned locations in the target region at which ultrasonic data is to be acquired is created, and a visual representation of the model comprising a plurality of graphical elements is displayed. Ultrasonic data at each of the planned locations is acquired. A transformation of the visual representation is executed, comprising: performing a data quality test at each target location; for any target location that fails the data quality test, altering a graphical element corresponding to the failed target location to indicate failure of the data quality test at that location; and displaying a transformed visual representation comprising updated graphical elements on the visual display.

20 Claims, 14 Drawing Sheets

(51) Int. Cl.
*G06T 7/00* (2017.01)
*G09B 23/28* (2006.01)
*G16H 30/00* (2018.01)
*G16H 30/20* (2018.01)
*G16H 30/40* (2018.01)
*G16H 40/00* (2018.01)
*G16H 40/67* (2018.01)
*G06F 19/00* (2018.01)

(52) U.S. Cl.
CPC .......... *A61B 8/5207* (2013.01); *A61B 8/5223* (2013.01); *A61B 8/565* (2013.01); *G06F 19/321* (2013.01); *G06T 7/0012* (2013.01); *G09B 23/286* (2013.01); *G16H 30/00* (2018.01); *G16H 30/20* (2018.01); *G16H 30/40* (2018.01); *G16H 40/67* (2018.01); *G16H 40/00* (2018.01)

(58) Field of Classification Search
CPC ......... A61B 8/467; A61B 8/52; A61B 8/5207; A61B 8/5215; A61B 8/5223; A61B 8/582; G09B 23/286; G06T 7/0012; G16H 40/00; G16H 40/40; G16H 40/60; G16H 40/67; G16H 15/00; G16H 30/00; G16H 30/20; G16H 30/40; G06F 19/30; G06F 19/32; G06F 19/34; G06F 19/3418; G06F 19/321
See application file for complete search history.

(56) References Cited

U.S. PATENT DOCUMENTS

| | | | |
|---|---|---|---|
| 8,630,867 B2 | 1/2014 | Yoo | |
| 2005/0228276 A1 | 10/2005 | He et al. | |
| 2007/0167705 A1 | 7/2007 | Chiang et al. | |
| 2007/0239004 A1* | 10/2007 | Kakee | A61B 8/06 600/437 |
| 2009/0169074 A1 | 7/2009 | Avinash | |
| 2010/0121156 A1 | 5/2010 | Yoo | |
| 2011/0190629 A1 | 8/2011 | Guenther et al. | |
| 2012/0238875 A1 | 9/2012 | Savitsky et al. | |
| 2012/0243757 A1* | 9/2012 | Funka-Lea | G06T 7/0002 382/131 |
| 2013/0296707 A1* | 11/2013 | Anthony | A61B 8/13 600/459 |
| 2015/0320399 A1* | 11/2015 | Chono | A61B 8/5223 382/131 |

OTHER PUBLICATIONS

Rohling, 3D Freehand Ultrasound: Reconstruction and Spatial Compounding, Churchill College Department of Engineering, Sep. 1998, pp. 1-158 (PDF is 184 pages).

Banker et al., "Interactive Training System for Medical Ultrasound," 2008 IEEE International Ultrasonics Symposium Proceedings, 978-1-4244-2480-1/08, 2008 IEEE, pp. 1350-1354.

Website: http://kpiultrasound.com/4D-ultrasound-machines/View-all-products.html, retrieved Dec. 12, 2013.

Fenster, Downey and Cardinal, "Three-dimensional ultrasound imaging," Phys. Med. Biol. 46 (2001) R67-R99 (www.iop.org/Journals/pb PII: S0031-9155(01)12089-0).

Goldsmith et al., "An Inertial-Optical Tracking System for Portable, Quantitative, 3D Ultrasound," 2008 IEEE International Ultrasonics Symposium Proceedings, pp. 45-49.

International Search Report issued in PCT/US2014/069862 dated Apr. 13, 2015.

Written Opinion issued in PCT/US2014/069862 dated Apr. 13, 2015.

International Preliminary Report on Patentability issued in PCT/US2014/069862 dated Jun. 21, 2016.

* cited by examiner

PROR ART

METHOD FOR ACQUIRING ULTRASONIC DATA

RELATED APPLICATION DATA

This Application claims priority from U.S. Provisional Patent Application Ser. No. 62/040,007, filed 21 Aug. 2014, which in turn claims priority from U.S. Provisional Patent Application Ser. No. 61/918,664, filed 20 Dec. 2013, titled "APPARATUS AND METHOD FOR GUIDANCE IN DISTRIBUTED ULTRASOUND DIAGNOSTICS," which applications are each incorporated by reference herein in their entirety.

BACKGROUND OF THE INVENTION

1. Field of the Invention

The present invention relates to the field of diagnostic non-invasive imaging and particularly to ultrasound imaging.

2. Background of the Art

Ultrasound imaging is a well established procedure in a wide variety of conditions, including its use for examination of fetal and maternal health during pregnancy. There are established procedures for training personnel, both in the acquisition of images with hand-held ultrasound transmitters, and in analyzing them for diagnostic as well as metric purposes. Standard metrics such as fetal dimensions and derived parameters help quantify fetal health and other diagnostic issues. In addition, there is continued effort to develop computer code that can automatically analyze an ultrasound image scan to compute these metrics, though the use of such algorithms is not yet widespread. Such code, while it automates the determination of the metrics from the images, does not in any way diminish the need for skilled operator acquisition of the images themselves.

The introduction of high quality ultrasound scanning equipment that can be attached to personal devices such as smartphones and tablets raises the potential for widespread dissemination of scanning technology, in particular to remote and rural areas. Developing countries including those in the Indian subcontinent, Africa, and elsewhere could become major beneficiaries of the technology. However, two factors in particular militate against this expansion in use and benefit: training needs, and (at least in India) heavy regulation against the possibilities for misuse. We here describe and add to the system referenced above, in the context of these factors and the way the system enables wider use of ultrasound in training, screening and the guidance of therapy. Its use thus has the material consequence that many more patients (particularly in a rural setting) may be referred for treatment, and may be treated more accurately, than might occur with current technology.

It is desirable to be able to provide an ultrasound-using health system for significant investment in the training of personnel to acquire suitable scans, which can then be read by experts to arrive at conclusions. (While it is possible for an expert to acquire a scan directly, the expert's time is a limited and costly resource, best not used in acquisition, where travel and other capital and personnel costs are required.) Particularly in developing countries, there is a lack of well trained personnel in the field. A newer generation of ultrasound machines has made the skill of acquiring good ultrasound images more readily teachable to people without prior skills. However, these imaging procedures depend on the operator's training in obtaining images, what to look for in the images, and ensuring that the result is a scan interpretable by skilled diagnosticians. While the learning curve is becoming shorter, imaging results remain highly dependent on training human visual interpretation of the images displayed from an ultrasound scan.

The Necessity of Anatomical Guidance in Current Practice

The present invention aims, not to improve anatomically oriented training, but to completely remove the necessity for the trainee to learn internal anatomy and its use in guiding image acquisition. However, as background, we discuss in further detail why the existing practice demands anatomical knowledge, and hence acts as a training bottleneck, with some further consequences considered below. Some hardware elements of existing practice are adapted for use in the present invention, making their availability important, so we give specific examples here.

FIG. 1 shows an exemplary instance (discussed in more detail below) of how training is commonly performed within the scope of current practice. Under the supervision of a trainer 104, the trainee 103 operates a scanner 102 on the body, or part of the body, 101 of a patient. This scanner or probe comes in a variety of embodiments from linear probes to curved linear arrays, phased arrays and volume probes. We are concerned here primarily with the so-called B-mode (brightness mode) or 2D mode of ultrasound, in which a linear array of transducers simultaneously scans a plane through the body that can be viewed as a two-dimensional image on screen, but other modalities (such as three-dimensional ultrasound imaging, for which software and apparatus are commercially available) exist in current use and may be adapted within the spirit of the present invention. Two-dimensional, hand operated ultrasound imaging has a long history, with key events such as the 1965 release of the Siemens Vidoson™ scanner, the first commercial B-mode scanner that operated in real time, producing a current planar display which could be used to guide a change of scanner position and hence of the acquired image. At the high end, a General Electric (GE) system which is fairly typical of the features available for this class of machines is the LOGIQ™ series, such as #7 and its associated transducers and probes. The use mode of guidance by watching the currently acquired image remains typical, and the present invention seeks to replace it. Although the invention does not seek to modify the functioning of the scanner itself, the process seeks to educate and train a local user in the art of appropriately changing the scanner positions used locally. In present practice the local operation of scanning equipment is managed by observing the images acquired. (In the present invention it is managed with the help of a tracker reporting location and position of the hand-operated components, and by other additions described below.)

Currently used in the same anatomy-guided manner are volume transducers, that, held in a single position, can capture data from material points not confined to a single plane, and thus generate a 3D image without further reconstruction. More complex and expensive devices can modify the plane somewhat without moving the scanner, or acquire 'volume' data from multiple planes simultaneously, such as in U.S. Pat. No. 7,758,509 B2, Multiple scan-plane ultrasound imaging of objects, Angelsen and Johansen, or see the review "Three-dimensional ultrasound imaging" by Fenster, Downey and Cardinal, Phys. Med. Biol. 46 (2001) R67-R99 (www.iop.org/Journals/pb PIE S0031-9155(01)12089-0) which remarks that "Although the integrated 3D probes are larger and heavier than conventional probes, they are usually easy for the operator to use. However, they require the purchase of a special ultrasound machine that can interface with them." A representative example has the product number 4D3C-L from GE. However, while this eases the task of anatomical guidance (since it is easier to recognize structures in a 3D image than in a slice), such local and hand-manipulated guidance is still relied upon in current medical usage. The requirements that the user know anatomy, and that the user sees the anatomical images, remain in place for actual diagnostic practices including technician acquisition of the image data. In the description below of the present invention, we disclose how these requirements may be avoided.

Also available from GE is a scanning system and probe that is more likely to fit within the scope of application of this invention in developing countries. This is the handheld VScan™ pocket ultrasound. Other manufacturers have competing products with different names and model numbers, and these could equally well serve as examples of commercially available system for use in the present technology.

In training or in regular use, the scanner 102 is normally placed in contact with the abdomen (or may be inserted into a body cavity) or other area where diagnostic or training imaging is to be performed, with sufficient coupling for good transmission of ultrasound, and collects data from echoes in a region 112 which has a shape and spatial relation to the scanner 102 which is fixed by the scanner design. As trainee 103 displaces or rotate the scanner 102, along or about any axis, the region 112 moves and turns correspondingly. (Most commonly the region 112 is a planar 'partial fan' as shown, though the more sophisticated scanners may without a change in device position acquire data from echoes in multiple planes, thus forming a directly volumetric scan, as mentioned.) The data obtained from the region 112 are fed via a wireless link or wire 111 to a computer 113, here shown as outside the casing of the scanner 102, though in general this need not be the case. Wireless is making rapid advances at the present time, and even particular protocols are quickly increasing their bandwidth capabilities. Furthermore, the concept of software-defined radio, exemplified in the open source GNU radio (allowing kilobits per second transmission) or Microsoft's SORA™ system supporting many megabits per second allow software and algorithmic advances to be immediately incorporated in contrast to more conventional application-specific integrated circuit (ASIC) or field programmable gated arrays (FPGA) approaches. It is sufficient for the purposes of this invention that conventional mobile telephone links be available, but the link to the computer from the scanning device can easily follow Wi-Fi (or more technically the IEEE 802.11 protocol) allowing much higher bandwidths. The computer 113 converts the ultrasound echo data to an image (by commercially available software provided by the ultrasound manufacturers with their systems) which is displayed conventionally via a link to a display unit (also referred to herein as monitor) 105 which may or may not be integrated or attached with a hand-held scanner 102 and/or the computer 113 which converts echo data usually to a planar image 106, displayed on a monitor or similar device 105. We do not discuss in detail the display units used in current practice, since first, the local display of the image data is preferably avoided in the present invention (we describe in more detail below the display that the present invention does use), and second, the units are just conventional screens available on smart-phones, laptops, and the like and can range in size from the handheld such as the GE VScan™ pocket ultrasound to 'desktop' units like the GE LOGIQ 7™, both already mentioned. The processing of echo data to form images is conventional and includes both analog and digital processing steps, such as described for example in Chapter 1 of the open source book "Ultrasound Imaging" edited by Masayuki Tanabe and published by Intech, 2011: http://www.ti.com/lit/an/sprab32/sprab32.pdf online) or in fast general purpose processors.

Both the trainee 103 and the expert trainer 104 can view the planar image 106 (if the trainee is given authorization to view the image), shown as a sector scan in the fixed plane of the display unit 105, rarely in the same direction of gaze as the scanner 102 for either trainee 103 or expert 104, and almost never in the moving orientation of the acquisition region of the body 101. (This mismatch, also typical with the more advanced volume scans, greatly increases the cognitive difficulty of their tasks.) The expert then may (verbally or by text to a local view screen) instruct the trainee to look for characteristic landmarks in the planar image, to arrange that a single planar image 106 should suffice for a particular clinical purpose. For example if the angle of, and the pressure applied to, the scanner is not ideal relative to the disposition of the fetus, then characteristic features used in metrics that indicate fetal health, may not be visible. The expert suggests alteration of the angles and the positioning of the probe in general, so that a useful scan may be obtained. Similarly, judgment of the anatomical position of the planar image 106 is needed to move the scanner 102 so that a single planar image 106 clearly reveals an appropriate slice of the femur (as an example of a diagnostic or training target, shown in FIG. 2 and discussed further below). Software may be used to provide automatic corrections based on automated image analysis for orientation and operation of the distal sensing devices, but as long as the goal remains optimality for one or more discrete slices, it is hard to operate without human judgment, and individual skill transfer of such judgment from expert to trainee, because anatomical clarity plays a large role in defining such optimality.

FIG. 3 shows the above-described current training process as a more abstract workflow. The scanner 302 interacts 308 with the patient or model 312, using echoes to obtain data related to material in its collection region 301. These data are processed to a greater or lesser degree, and communicated 311 to the computer 313 which continues the processing, resulting in a digital image which is passed 310 to the monitor or similar device 305 which displays it. This is observed 315 by the trainee 303 and 317 by the expert 304, who gives 316 spoken or text advice to the trainee 303, who modifies 323 the location and orientation of the scanner 302 accordingly, and the workflow continues on the same paths. The Figure does not include the trainee's mental models for patient anatomy, quality of images, etc., or the learning process by which these are created and improved.

In the existing practice this process of training is continual, typically continuing beyond the specific training and licensing period into actual practice. The trainee or neophyte operator acquires the requisite skills by a learning process that is largely based on an expert (local or remote) distinguishing 'good' scans from 'bad' ones and relaying approval and corrections to the trainee. We illustrate this with an example, to elaborate on the point that the distinction is not merely technical (with such criteria as resolution and level of distortion, expressible in engineering terms) but anatomical, requiring real anatomical expertise on the part of the operator: even if the operator is not responsible for diagnostic or clinical decisions, or advice to the patient, this expertise is required for the acquisition of clinically useful slice images. Our example is the particular fetal parameter of the length from end to end of the femur (the thigh bone, longest in the body): similar considerations apply to other fetal parameters, and to many non-obstetric applications of ultrasound. To acquire a slice image that will be useful in estimating femur length, the user must understand the anatomy of that moderately complex bone (FIG. 2). The parameter is defined as the distance along the femur shaft 201, and should not include the secondary bone forming center at the more complex end. To assess this by means of a planar image requires that the image plane intersects the bone similarly to the plane 221 (shown sideways as a line, as if from the scanner head) or to one rotating the plane 221 about the poorly defined axis of the curved shaft. The femur of a fetus may present in any orientation, depending on fetal posture, and many planes are impossible for scanning from points on the abdominal surface, so the operator must select a full lengthwise slice from what is achievable and do it using only what is visible within the slice. The knob 250 to one side is not visible when the slice is correct, and a slightly oblique slice can miss one end or the other. Even a technician who is not tasked with the measurement itself must understand the femur length parameter well to produce images from which it can reliably be estimated.

It is equally problematic to estimate the length of the humerus (a smaller and more delicate bone though geometrically slightly simpler), and parameters such as head circumference, occipitofrontal diameter and abdominal circumference are even more difficult. Only anatomical understanding, and substantial experience of what an acceptable slice looks like, can produce a high proportion of good images: similarly for diagnostic images of the liver, gallbladder (such as gallstones), pancreas, thyroid gland, lymph nodes, ovaries, testes, kidneys, bladder and breast. For example, it can help to determine if an abnormal lump in one of these organs is a solid tumor or a fluid-filled cyst, or detect abnormal widening of blood vessels. A newly qualified technician in the field creates more 'bad' images than an experienced one, reducing the efficiency of the system, but only on-the-job continued learning, with continued feedback from experts, produces the final level of skill. (The non-quantitative distinction between male and female fetus is more easily learned and practiced.)

The present invention does not aim to provide the operator with feedback on the quality of planar slices, in the above sense of diagnostic quality: to do so would require replacing the expert's anatomical judgment with artificial geometrical intelligence at a higher level than has yet been shown achievable, and would at most improve training in the classic, anatomy-guided process. The aim is to completely replace the anatomical criteria on acquired slices, reducing the cognitive task, the required training, and the educational level required of a trainee, all of which are bottlenecks in the dissemination of ultrasound diagnosis, particularly in less developed countries. At the same time, it avoids a major problem with current practice, described next.

The Informational Consequences of Local Access to Images

We have seen above that visual feedback is necessary in the current system, if the operator is to acquire good images. Since that feedback involves anatomical knowledge, it creates a bottleneck of available ultrasound operators and a difficulty in training more, but there is also a problem with the fact that such feedback requires that the device be operated by somebody who from moment to moment, sees its output as an anatomical image. This causes a significant obstacle to dissemination of the new generation of highly portable cheap scanners. We refer particularly to India, but the problem is widespread. There are groups who use ultrasound imaging to determine sex, as a means to selectively abort (in particular) female fetuses. India's 2001 census revealed a ratio of 126.1 male births to 100 female in the Punjab, showing that many parents had practiced selective abortion: but statistics give no clue as to which parents did so. The birth of a son, or several sons, in one family is not evidence of an aborted daughter. To limit this use of ultrasound technology, India has laws that disbar physicians or medical personnel who inform parents of the sex of the fetus. However, if a local operator or clinical worker can see the images of a fetus, that person can be bribed to reveal the sex. To attack that problem, the Indian government has also severely restricted the deployment of ultrasonic imaging equipment for any purpose whatever, particularly in remote areas, outside the larger and more controllable clinics. In several states, the sale of portable ultrasound is a criminal offence, because it can abet in the crime of sex determination. These restrictions render the technology unavailable for ethical diagnostic purposes, even those unrelated to pregnancy, and prevent both businesses and non-profit organizations from supplying ultrasound services in many areas of India and other countries.

If the rural operator could acquire clinically useful data which is then transferred to a controlled clinic, using equipment that does not enable the operator to access images that reveal fetal sex, such restrictions would be unnecessary. However, since the present system requires that the operator sees the current image (in order to use anatomical awareness to improve it), it cannot simultaneously blind the operator to fetal sex.

A similar problem arises with the privacy of such images: while most countries have privacy laws restricting the availability of patient information (the Health Insurance Portability and Accountability Act of 1996 in the US being a notable example), the more people see a medical datum, the greater the risk that it is shared improperly. This is particularly true in small communities, where a patient may be personally known to an operator.

Thus there is a need to develop a method that ensures widespread dissemination of the technology and its use for the benefit of people, and at the same time, avoids use of the technology for unethical purposes. The invention described in the above disclosure, and its extensions here disclosed, avoid the use of anatomical awareness in navigation. This not only simplifies the task (as noted above) but enables the acquisition of image data while maintaining their security against local knowledge, and hence of improper use of such knowledge. This has evident medical, social and business advantages.

Three-Dimensional Reconstruction in Current Practice

If the instantaneous position of the scanner is tracked by an attached tracking device, parameters obtainable from the scanner specifications allow computation of the planar extent and position of a scan from a specific location of the scanner. The volumetric scan required is then obtainable from a succession of such planar scans, without requiring that these be parallel or move by uniform translation, which would be more easily achieved by a robotic system than by a human. There are many means of achieving a volumetric data set from such data. In illustration, we observe that every intensity level at every pixel in each image can be 'splatted' to an (x, y, z) position in the display coordinate space, analogous to the splatting of ray values into a 2D image described in Westover, SPLATTING: A Parallel, Feed-Forward Volume Rendering Algorithm, doctoral dissertation, UNC Chapel Hill 1992. Combining these splats, by blending and interpolation, one can construct an array of intensity levels I(i, j, k) which can then be manipulated using standard techniques for 3D scans by CT, MRI, etc., which are engineered to produce data in this format. See for example the PhD thesis 3D Freehand Ultrasound: Reconstruction and Spatial Compounding by R N Rohling; but it is typical that for instance the paper Freehand 3D Ultrasound Calibration: A Review, by Hsu, Prager, Gee and Treece, CUED/F-INFENG/TR 584, December 2007, which discusses accuracy in some detail, does not consider guidance of the user. A web site reviewing scanning products, (http://kpiultrasound.com/4D-ultrasound-machines/View-all-products.html, retrieved 12 Dec. 2013) remarks that Freehand™ 3D "requires operator skill and hand movement to do the 3D scan". Such skill is hard to acquire if the operators' use of the scanner is guided by the anatomical images: the present invention also uses three-dimensional reconstruction from a series of planar scans, but provides guidance whose use is easier, and easier to learn. This has the material effect of shortening both use and training, increasing the pool of potential trainees by reducing educational prerequisites, and (with appropriate funding) increasing the actual number of qualified operators beyond what is practical with current methods.

In the system disclosure referenced above, an operator manipulates an ultrasound scanner, guided not by a display of the image it is currently collecting but by a geometric view of where the image is being collected, as in the shaded polygon 555 in FIG. 5. This polygon 555 moves in geometric correspondence to the acquisition region of the scanner, with the requirement of sweeping through an indicated volume of interest such as 505. It is not of the essence of the invention that only geometry be displayed, though this is an important option in concealing from a local operator the imaging details acquired, to avoid revealing fetal sex. The display of 3-dimensional geometric guidance in motion of the sensor is central to the invention: the un-usability of the system for sex determination, in certain implementations, is one of the more important options that it makes possible.

USPTO Patent Application 20090169074, System and method for computer assisted analysis of medical image addresses the sex revelation problem by selective blurring. The performance of such selection requires complex real-time image analysis connected to the device, identifying by one means or another (many are listed as possible) the anatomical region to be masked. It is not trivial in a two-dimensional anatomical slice to identify what is on view (even for a human observer), and to the best of our knowledge the particular task of recognizing fetal genitalia in real time in such scans has not been accomplished. This task is not called for, either in our application referenced above, or in the extension here disclosed.

We note also the literature on 3D reconstruction of a scanned tissue based on the tracked motion of a sensor: see for example "An Inertial-Optical Tracking System for Portable, Quantitative, 3D Ultrasound" by A. M. Goldsmith and P. C. Pedersen, 2008 IEEE International Ultrasonics Symposium Proceedings, pp 45-49, and references therein. We do not here claim innovation in the algorithms by which the reconstruction is performed, but in the method by which the operator of the sensor is guided. The paper "Interactive Training System for Medical Ultrasound" by C J Banker and P C Pedersen illustrates well the current method of guidance, by visual anatomical feedback imaging the interior of a real or virtual patient: the twin disadvantages of this are the considerable training required, and the (less demanding) utility for fetal sex determination, which in some situations is illegal. The present invention offers more easily mastered geometrical guidance, which by not displaying the patient's internal anatomy simplifies both the task and compliance with local legal requirements.

As further background, we here recapitulate a summary of the above disclosure, before reciting a brief description of the present extension to it.

SUMMARY OF THE INVENTION

We here describe various additions and possible modifications to the invention previously disclosed and described above, with particular emphasis on the manner of local display and transfer of data.

In a first such variant, the currently acquired image is displayed in situ in the geometric view shown in FIG. 5, as a 'texture' added to the moving polygon 550, rather than as a flat view in an unchanging position on a display device. If this view is so oblique as to obscure significant details, that the operator wished to see in real time, a 'laid flat' display unit 105 as in current practice may be added.

In a second such variant, the currently acquired image is displayed in the same real-time way as a texture on the polygon 150, in the same apparent location, but sufficiently blurred (throughout) that detail of the scale of fetal genitalia can nowhere be seen.

In a third such variant, geometric features including but not limited to boundaries between light and dark areas are extracted from the current image data by means well known to those skilled in the art, without an attempt to attach to them an anatomical meaning (such as 'edge of a fetus leg region'). If such an extracted boundary is long and smooth, with few corners or sharply curved regions, it cannot represent the surface of fetal genitalia, and may thus be shown in a polygon 150 or 210, or both, without revealing fetal sex but assisting the operator in anatomical judgment of the scanning location.

In a fourth such variant, a preliminary analysis of the echo data locates points whose sound reflections are sufficiently strong, relative to the other echoes currently received, to imply that these points are occupied by bone or other hard material. These points are added to the display.

In a fifth such variant, features such as those described in the third or fourth are displayed in superposition on the blurred image shown as described in the second variant above.

In a sixth such variant, numerical measures are applied to the acquired image data, revealing whether they are suitably sharp. If they are not, the region within the target box of the display unit 105 where better data are needed can be three-dimensionally marked (by a smaller box, or other graphical means familiar to those skilled in the art) as requiring a repeat visit by the region 112 acquired by the scanner.

In a seventh such variant, numerical measures are applied to the acquired image data, revealing whether their planes are sufficiently closely spaced for the reconstruction of a volume data set. If they are not, the region within the target region of interest 505 where better data are needed can be three-dimensionally marked (by a smaller polygon 555, or other graphical means familiar to those skilled in the art) as requiring a repeat visit to the region 112 by the scanner.

In an eighth such variant, the sensing system is capable of Doppler analysis, for example giving indications of maternal and fetal blood flow along the line of 'view' by frequency changes in the echo. Since other directions are often important, data collection requires varying the direction as well as the point with respect to which data are collected, in a manner described in more detail below, giving a fuller reconstruction of flow than is possible with image acquisition in a single plane. The system applies numerical tests for the confidence values of this reconstruction, and displays the results in a polygon 550 or 810, or both, to guide rescanning.

A ninth such variant allows for movement of the target during the scan, such as a fetus may do, by fitting the motion of bones to an overall model of motion, and using this to correct for artifacts of movement.

A tenth such variant allows for more regular and limited motion, such as that of the heart. In this case the motion is unavoidable, but periodic rather than unpredictable. Collecting the scan data together with time stamps and the output of at least one electrocardiogram or other pulse-related sensor, and assuming regularity of the motion, we collect echo data for a sufficient density of points $(x, y, z, \Phi)$, where $(x, y, z)$ represents spatial position and $\Phi$ is cardiac phase. The acquired image is thus four-dimensional (giving either scalar echo strengths or vector flow data), and the repetitive nature of heart motion means that gaps can be revisited.

In an eleventh such variant, the three-dimensional image reconstructed is used for the automatic analysis of anatomical structures such as a growing femur, including quantitative comparison with growth norms, objective sex identification to be non-erasably stored (permitting correlation of a clinical institution's records with later abortions, to raise statistical warning of security leaks), identification of structurally important features, and for certain conditions (such as identification of conjoined twins, mis-positioning of a fetus within the womb, or inappropriate arterial connections in an adult or immature body) identifying plans of treatment.

DETAILED DESCRIPTION OF THE INVENTION

Figure 1:
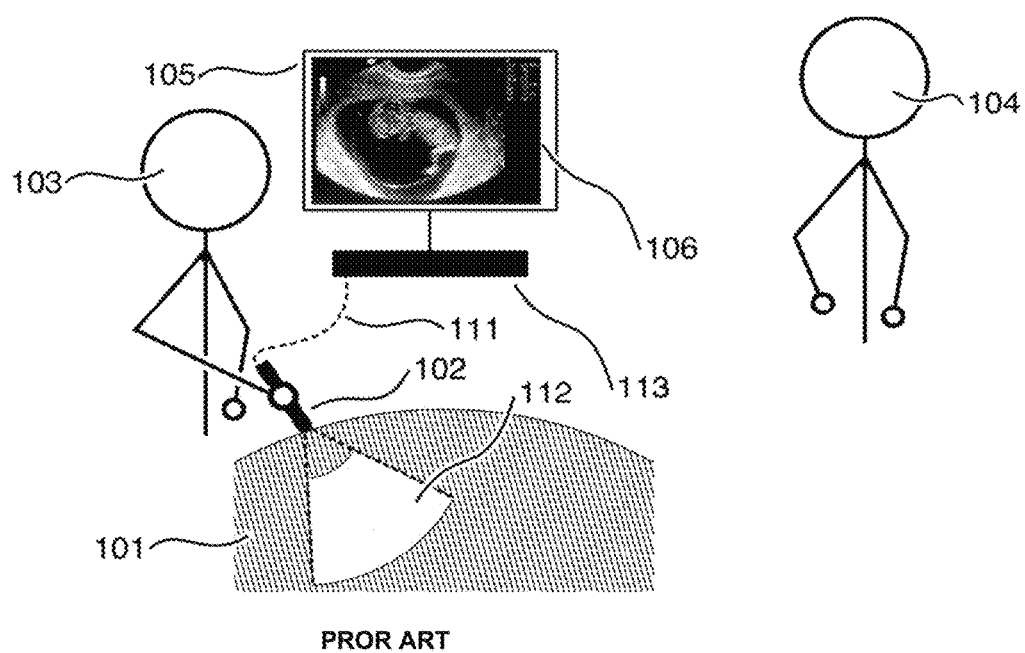
FIG. 1 is a representation of conventional training of personnel and the use of apparatus in the acquisition of scanned ultrasound images for health monitoring including fetal health monitoring.
Figure 2:
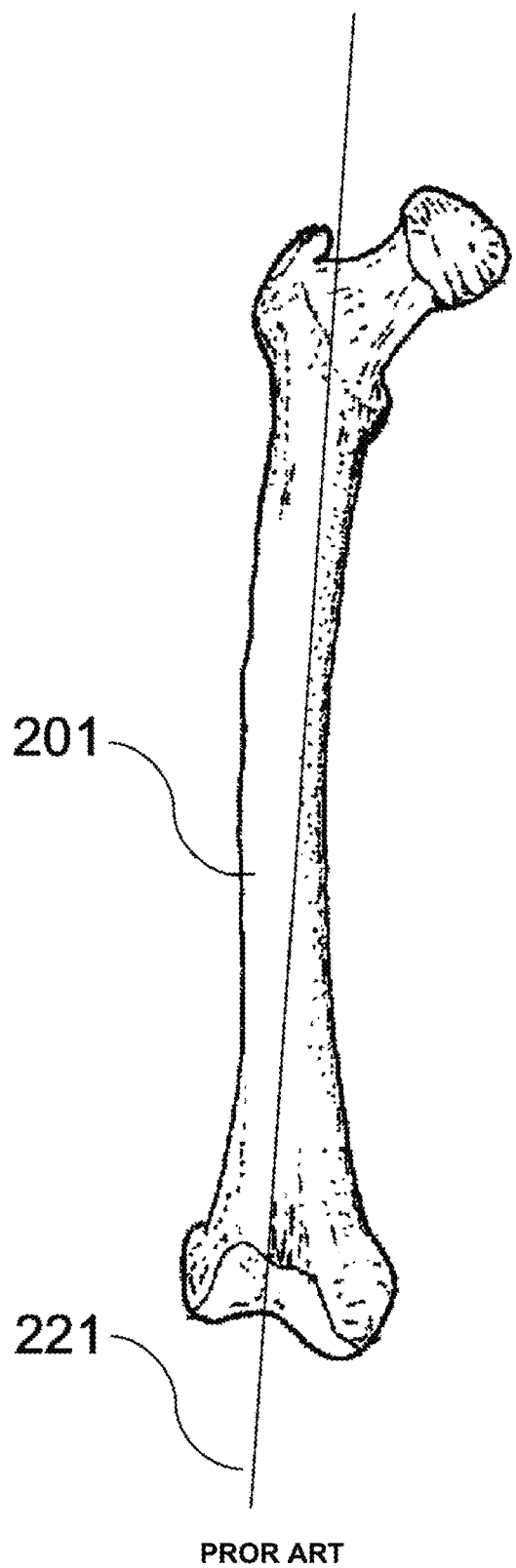
FIG. 2 shows a femur and an imaging slice orientation which permits estimating its length.

Our invention is directed towards both the problems above, of training needs, and legal restrictions against the possibilities for misuse: the need for skill in acquiring satisfactory images by visual inspection and anatomical evaluation, and the consequent necessity of visual access by the operator, with attendant risks of selective feticide and loss of privacy. By blinding the local user to the images, distal qualified medical personnel may retain control over diagnoses and the images for business and professional purposes as well as legal and billing requirements.

This technology enables a method, system and apparatus to de-skill the requirements for the 'field operator' who manipulates the ultrasound equipment to acquire the images, reducing both the prerequisite level of education, and the time and cost of training. Further, implementations of this method can be easily adapted to prevent unauthorized people (including the local field operator) from viewing, sharing or analyzing the images.

The training of field operators requires no more technology than that within a simple 3D video game. The training may be provided in a relatively brief period, with appropriate feed-back through processes and systems described herein. Both the use of the method and apparatus, and the necessary training, can thus cost less than for current methods, and importantly can be widely deployed in remote areas. (Wired or wireless web access is a necessary condition for deployment of the analysis component, although high bandwidth and lack of interruption are not critical to the performance of the method.) Furthermore, in contrast to existing training methods, the present invention for training does not require the acquisition or display of any patient images to the field operator, because when working with a patient the field operator will see only computer-generated 3D geometric constructs. As noted above, the absence of locally viewable actual images of a patient is one optionally desired objective of the present technology, especially in jurisdictions where such local sharing may be prohibited by law. In consequence, in its deployed version, the technology can simply omit the system elements required for local display, or a further layer of technology can actively prevent (for example by encryption) display of the images to the field operator. The technology does not exclude that the system be physically equipped for local viewing, in which case it may be provided with a distal command that can deny or block local image capability: however, this capability raises the hardware costs of the system, and offers a weak point to security in that an engineer who can disrupt such blocking (by modifying communication with the distal computer, by local interference with the command, or otherwise) then opens the entire local system to display of the acquired images, without hardware changes. Where security is important, therefore, in our preferred embodiment the local, on-site system excludes entirely the capability to display image data captured from the ultrasound sensor. It is necessary, as described below, to have a visual display system that can show (with one or more depth cues to a human viewer) a three-dimensional geometric outline of the volume for which data are to be acquired, and a flat polygonal structure whose position represents the three-dimensional position of the planar region for which the sensor (as currently located) can acquire images. It is not necessary to display any anatomical information, either simulated or acquired from the current patient, in direct form or enhanced as in A Virtual Reality Patient and Environments for Image Guided Diagnosis, by Takacs, Hanak and Voshburg, Medical Imaging and Augmented Reality, 279-288: the concern there is to show the anatomy more clearly, whereas the object here is to avoid all need to show it. In our preferred embodiment, no such information is shown.

Figure 4:
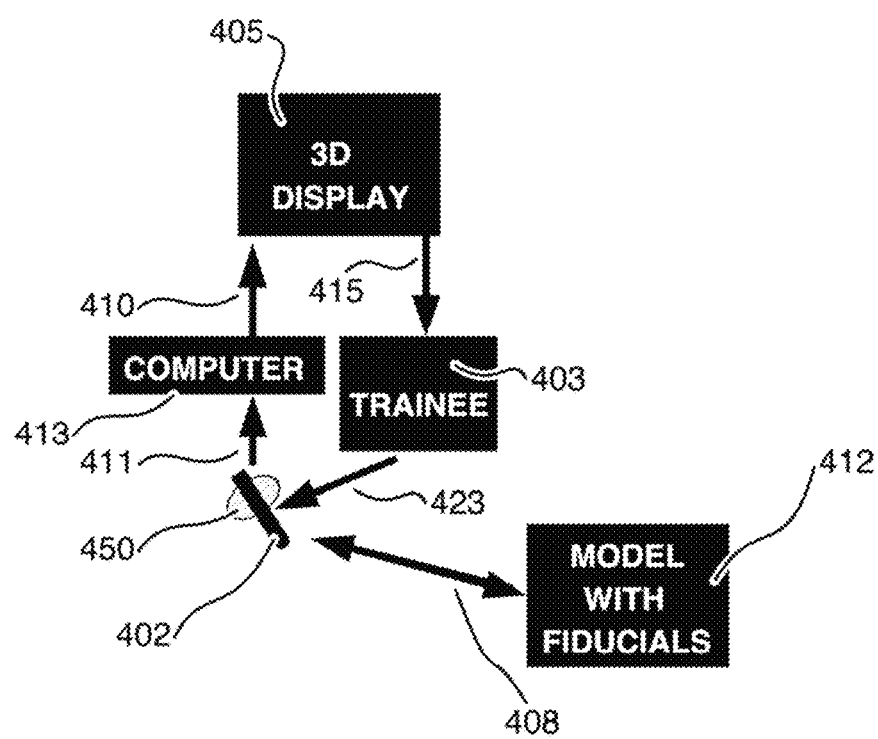
FIG. 4 is a schematic representing the information flow associated with training in the use of the present invention.

This lack of need for anatomical display in guidance enables confining such displays to authorized centers for diagnostics, while the geometric display described below provides both training to potential local users and guidance to actual local users, without requiring that the actual user sees any anatomy or (hence) that the trainee needs to see any anatomy, real or simulated. Technologically and administratively secure procedures can then safeguard reservation of the use of such imaging to ethical and beneficial purposes. Furthermore, the framework of data acquisition concurrently with 6-degree-of-freedom data for the ultrasound device makes possible the reconstruction from individual images (in our preferred implementation, planar images) of a 3-dimensional model of the scanned anatomy, if the acquired planar images collectively satisfy appropriate geometric criteria (rather than individually satisfy anatomical criteria), and hence the quantification of diagnostic measures from such a 3-dimensional model. Unlike the current anatomical criteria, the geometric criteria can be straightforwardly quantified using only tracking information, so that a computer can provide feedback to a user or trainee without analysis of the acquired images, as to whether the geometric criteria have been met. This has advantages in simplifying and improving training and use, even where security is not a concern. FIG. 4 shows the flow of the simplified training process enabled by the current invention.

In one preferred embodiment, the system uses only a moving scanner that can acquire a planar image, in a fixed position relative to the scanner, rather than the volumetric scanners mentioned above. These more costly systems could be used, and their output could be locally hidden in the same way, with minor modifications of the reconstruction and display performed distally, as will be apparent to those skilled in the art. However, since the present invention includes 3-dimensional reconstruction and distal 3-dimensional display, the relative advantage of such systems is less than in it is in anatomy-guided practice. (It is true that to capture the motion of a structure such as the heart, a sequence of volumes has greater value than a sequence of slices. Within the spirit of the present invention one could use such a sequence of volumes, acquired by geometrical rather than anatomical guidance, to construct a 3-dimensional movie.)

The use for scanning in pregnancy is a preferred application of the invention, which exploits both the reduction in required field skill and the option of restricting display, and we therefore use this for exemplary description. However, the extension to other ultrasound diagnostics (e.g., orthopedics, gastroenterology, and other ultrasound image-enhanced views of a patient), where a lack of skilled operators and the possibility of abuse are currently preventing a needed widespread dissemination of the technology, should be obvious to those skilled in the art.

The communication bandwidth requirements for the system are relatively modest. An uplink 670 (FIG. 6) to the cloud 680, and thence delivery 685 to the clinical display site (hereafter also denoted site) 690 where the images are to be read (or in a less preferred embodiment, a direct link from the computer 613 to the clinical display site 690) does not have to be 4G, since the images can be sent over a period of time provided they can be stored within the handheld device. The downlink requires even less bandwidth, since only a report of the diagnostic conclusion needs to be conveyed to the remotely located patient. Notwithstanding, faster bandwidth links are advantageous, and the use of the somewhat more modern space-time coding technologies such as multiple-input and multiple-output (MIMO) transmissions and its variants appropriate for this invention will be apparent to those skilled in the art.

Figure 7:
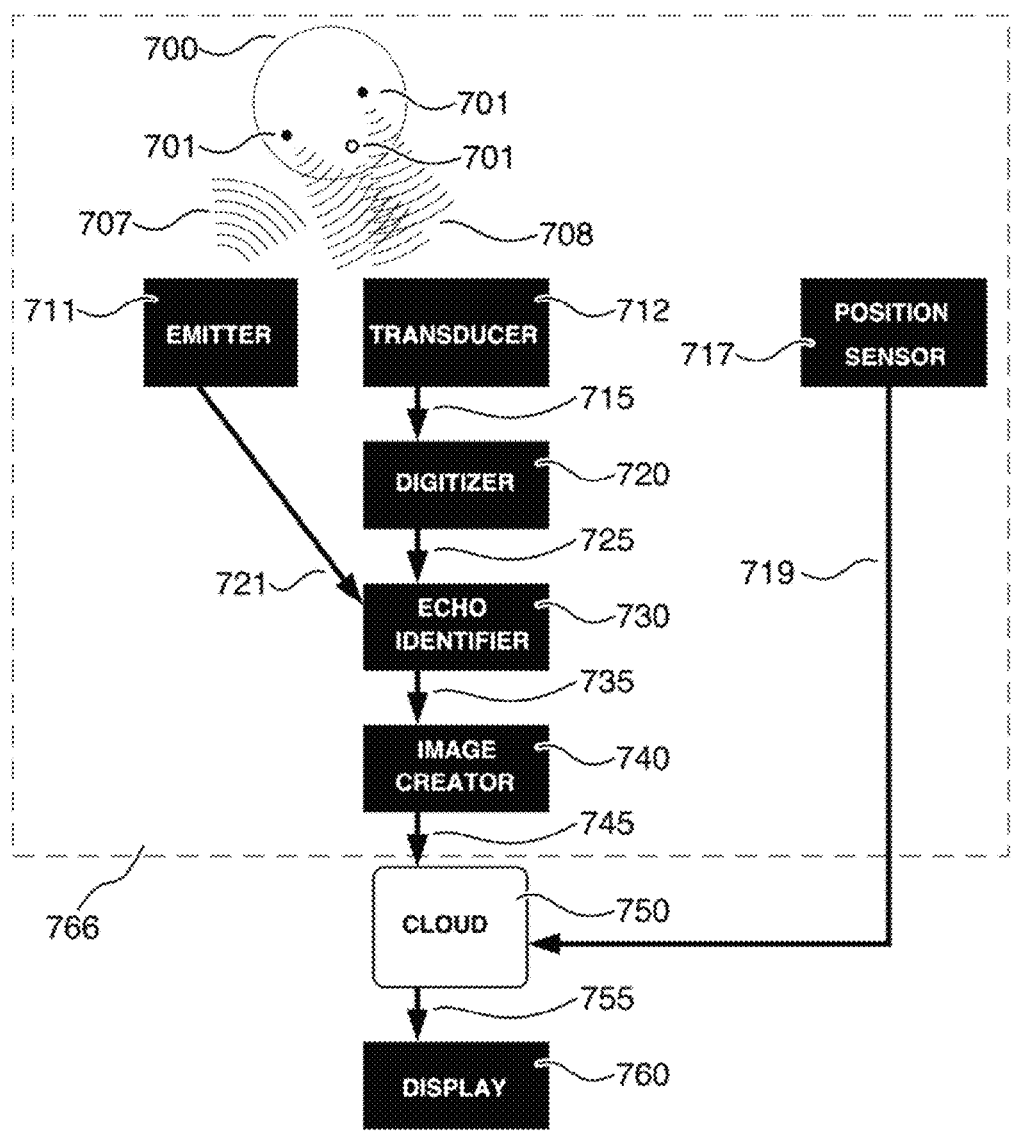
FIG. 7 is a flow diagram showing data flow in a process according to the present technology, and certain stages along the data flow where access by the local user may be enabled or prevented.

FIG. 7 summarizes the physical flow that creates the images finally shown, without reference to the guidance system. An emitter 711 creates ultrasound pulses which echo from structures 701 in the patient 700 and are detected by a transducer 712, converted to digital signals by an analog-to-digital converter 720, compared by an echo identifier 730 with the emitted pulses to detect echoes, and interpreted 740 as spatial reflectivity data by interpreting the echo delays as distances, and hence as 1-dimensional images along particular lines 530 from the sensor. In a particularly secure embodiment, these linear data are combined in the cloud 750 (outside the local environment 766) with positional information transferred 719 from the position sensor 717 attached to the emitter 711 and transducer 712, to give a 3-dimensional image made available to the remote clinician by a display 760. It is not required that even 2-dimensional images exist within the local environment 766. (Indeed, the echo data could be transferred directly from the echo identifier 730 to the cloud 750, but for bandwidth reasons we prefer to perform a limited spatial interpretation 740 locally.)

More briefly: A method of acquiring medical images (understood as including printed, hard-copy, visually displayed images on CRT, LED, Liquid Crystal or plasma devices, or datasets for automated evaluation of fetal metrics, severity of kidney stone disorders, or other uses) arranges that the operator acquires clinically useful images by following geometric criteria which can be verified by local computation, without reference to the images themselves for guidance. The computer determines these criteria with. reference to fiducials placed on the patient, according to a standard protocol for a particular condition (such as pregnancy) and displays geometric feedback on the device's motion sufficient for the operator to meet the criteria. The method has an on-site user manually operate a 3-dimensionally tracked non-invasive image device to produce image data. A computer (preferably on site) determines whether the motion revealed by the tracking implies that the acquired data are sufficient for the reconstruction of a 3-dimensional image array appropriate for further visual or automatic analysis, such reconstruction being in a preferred embodiment performed by a distal computer to which the image data are transmitted. Optionally, the computer reports to the on-site user an indication of image quality performance determined by the computer.

The apparatus and method may be used in training and in actual diagnostic practice in the field. The training and the field operation will be separately described. The description here uses obstetrics as an exemplary field of application:

other fields of application are enabled in a manner that will be obvious to skilled personnel.

Figure 3:
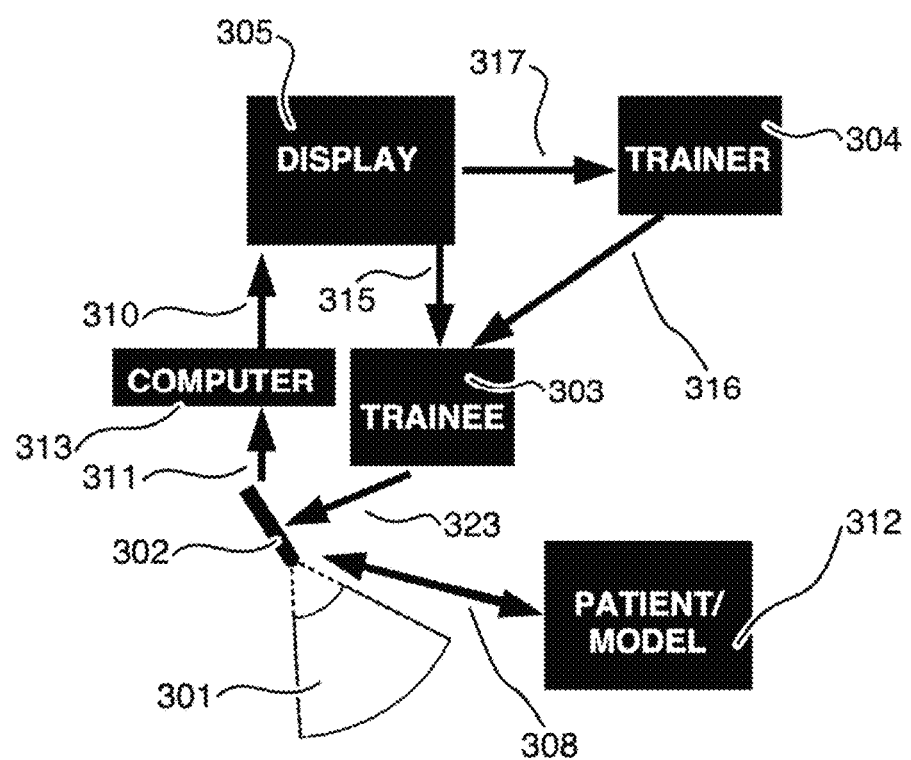
FIG. 3 is a schematic showing the information flow associated with conventional training as in FIG. 1.

In contrast to the current training method described in the Background and illustrated in FIGS. 1 and 3, in the system proposed by the present invention the training is performed according to the information flow in FIG. 4. It uses a geometric 3D display unit 405, rather than the 2D acquired image display on the monitor 305, and an expert trainer is not required (though supervision and advice by a more experienced person may be helpful, and is not excluded). The components in common with the conventional method are shown with similar numbers to FIG. 3, e.g., 413 for the computer 313 and so on. The patient in the conventional scheme may sometimes be substituted with a 3D anatomic model, including internal structures: the present invention requires only an external resemblance, with the addition of fiducials and a tracking system, as follows.

The scanning device 402 is equipped with a 6DOF tracker 450: a device which reports the device's current location and orientation (roll, pitch and yaw, or equivalent information) in a 'frame of reference' or system of coordinates (u, v, w). (Together, we call the location and orientation of the device its position.) Such trackers are well known to those skilled in the art, and may function in various ways (not shown): for example, included accelerometers may allow computation of the current position relative to an initial state (as in a 'Wii' remote): the necessary accelerometers, with software to derive positional data, are available separately from many sources, such as the ACC/GYRO, 3D, 16G, 2000DPS, 28LGA 6DOF Analog Inertial Measurement Unit (3 Axis Accelerometer+3 Axis Gyro) manufactured by STMicroelectronics in Bangalore. Alternatively, the tracker 450 may receive from a fixed base station electromagnetic signals that allow computation of the current position relative to the base station: the necessary hardware and software for integration into a system such as the present invention are available separately from many sources, such as the Aurora Electromagnetic Measurement System manufactured by Northern Digital Inc. in Waterloo, Ontario. Alternatively, one or more cameras may acquire images of targets incorporated in the tracker 450 that allow computation of the current position relative to those cameras: the necessary targets, cameras and software for integration into a system such as the present invention are available separately from many sources, such as the family of products manufactured by Iotracker™ in Vienna. Any device that obtains such information may be used within the spirit of the present invention. The tracker may be integrated with the design of the scanner, or a scanner already on the market may be incorporated into a casing that also supports a tracker. Modern examples of such scanners from major manufacturers such as GE, Siemens, and others can easily be obtained.

The fiducials are small objects or tracker detectable inks or markings for which the tracking system may be able to detect the location, as well as that of the moving scanning device 402, in the same (u, v, w) reference frame as is used in tracking the scanner: alternatively, the operator may 408 touch each of them with the tracked scanning device 402, in a prescribed order, indicating to the system by a click or other signal that the current device position defines a fiducial position. Their orientation data is not required. At least three such static fiducials are placed on the model patient, in anatomically standardized positions such as (by way of example) the navel, the anterior superior iliac spines, the pubic symphysis, prominent skeletal features, etc.; mostly skeletal landmarks that can be located by touch, with little training.

These positional data are reported 411 to a computer 413, perhaps from intermediaries which compute them from raw data, such as a base station, a computer connected to cameras, a separate program running within the computer 413, etc. Any means that produces equivalent result positional information may be used within the spirit of the present invention. The computer 413 creates a 3-dimensional image which it transmits 410 to the display unit 405 which is visible 415 to the trainee 403, who modifies 423 the position of the tracker 450, attached to the scanner, which is again reported 411 to the computer 413, and so on. It is desirable that the latency in this cycle be short, with a delay of the order of a tenth of a second or (preferably) much less.

The computer 413 could be a smartphone, tablet, or other computational device already available to the operator, or it could be or could include a special purpose chip which augments the said computational devices. The display unit 405 may be incorporated in the computer 413, as in a smartphone or tablet, or a separate unit, for increased resolution and field of view. In our preferred embodiment the orientation of the displayed image corresponds to that of the dummy model 412, and its location is near the same line of sight from the trainee's perspective as in viewing the model 412.

It is desirable to the invention that the image displayed is 3-dimensional, in the sense that it provides sufficient depth cues (such as one or more of occlusion, directional lighting, perspective, parallax, etc.) to be perceived by the trainee in three dimensions, rather than as a flat image. In our preferred embodiment, the image is displayed in stereo, thus including the specific depth cue of presenting a distinct view to each eye, from which normal human vision can triangulate distance. Such a presentation may use shutter glasses, which alternately blank the view of each eye in synchrony with a high-speed pixel display which alternately show the views intended for the left and right eyes. These, together with the necessary synchronization hardware and software, are available separately from many sources, such as the 3D system for both cinemas and small screen use manufactured by XPAND in Limassol, Cyprus. Most shutter systems can use any pixel-oriented display device, whether it is a panel of light-emitting diodes or phosphors or other digitally controllable light sources, a panel of liquid crystals selectively filtering a backlight source, a projector that casts a digital image onto a passive screen by similar filtering, or other such devices standard in the display industry, provided only that they support a high refresh rate (120 images/sec is desirable) as does the graphics board, which must also support the synchronization system. Such systems are widely available, with a preferred version manufactured by Nvidia in Santa Clara, Calif., integrated with its highly parallel graphics processing units.

Alternatively, the invention may use passive glasses, with the left and right eyes seeing through complementary polarizing filters (e.g., linearly polarizing in vertical versus horizontal directions, or circularly clockwise versus anti-clockwise). The two views are arranged to arrive with the corresponding polarizations (at a refresh rate on the order of 50 or 60 images/sec) from the display. This arrangement is most easily achieved in a projection system, where the left and right eye views are projected from standard projectors simultaneously through different passive filters, or alternately through a synchronized filter such as in the projection technology made and sold by RealD Inc., in Beverly Hills, Calif., widely used in cinemas. It has more recently been achieved at the display panel level by such methods as the systems introduced by manufacturers including TV makers LG and Vizio, with horizontal polarizing stripes overlaying the screen, though this halves the resolution available to each separate eye. With prices geared to the consumer market, this technology is incorporated in devices such as the MSI CX620 (MS-1688) 3D laptop. An embodiment of the present invention could use either such a laptop, or a separate screen obtained directly from the manufacturers.

Alternatively, the invention may use an autostereoscopic display, usable without glasses. Each pixel location in such a system creates at least two RGB color combinations, separately visible from different regions of space, so that if each eye is in a different region the eyes see different images: this requires the eyes to be approximately in pre-planned positions, since with current technology the regions cannot be changed on the fly. (More complex systems, with more than two regions, allow more than one pre-planned 'sweet spot' for the user's head.) Commonly, such displays use a system of small lenses (often vertical stripes) or a parallax barrier (with narrow vertical gaps through which the user sees different pixels form different directions) to confine the light from neighboring columns of pixels toward the target regions. A typical autostereoscopic system is the display of the laptop Toshiba Qosmio™ F755-3D290. Again, the present invention could incorporate either such a laptop or a separate display.

Alternatively, the invention may use a holographic display system, emitting a different view at every angle (not just at a small set of angles, like a lens-based autostereoscopic system). Holography is claimed to be used in the HoloVizio™ system manufactured by Holografika in Budapest, Hungary, perhaps in the manner disclosed in U.S. Pat. No. 5,801,761, Method and apparatus for displaying three-dimensional images, to Tibor Balogh, 1998. A real-time system for holographic display to a limited number of tracked eyes has recently become available from SeeReal Technologies S.A., of Luxembourg. We mention this approach here for thoroughness, though it is unlikely that holography would be cost-effective for a first embodiment of the present invention.

Alternatively, the invention may use the 'anaglyph' system with a different color filter for each eye (often red and blue) first described in 1853 by Wilhelm Rollmann, "Zwei neue stereoskopische Methoden," Annalen der Physik 166: 186-187. The anaglyph scheme is the most robust and least costly, requiring only a standard color display with paper glasses, and completely adequate for the present purpose (particularly if the filters are chosen to work well with the common forms of color blindness), and is thus our currently preferred embodiment.

All these methods of providing the stereographic depth cue can be combined with the parallax depth cue, where the visible image changes with the motion of the head and thus of the eyes. True holography already contains this cue, by emitting a different view in every direction, but the other displays can gain it (for a single viewer) by eye-tracking and computing the view shown using the current point(s) of view of the user or of the user's separate eyes. This is described in the paper C. Zhang, Z. Yin, D. Florencio, "Improving Depth Perception with Motion Parallax and Its Application in Teleconferencing," MMSP, 2009, and could optionally be included in the present invention, though it requires additional hardware (one or more cameras observing the eyes, or a trackable head mounted device), substantial local processing power, and high speed in all elements of the system to avoid distracting delays. This is an area of active research, but not yet robust enough for a preferred embodiment of the present invention.

Figure 5:
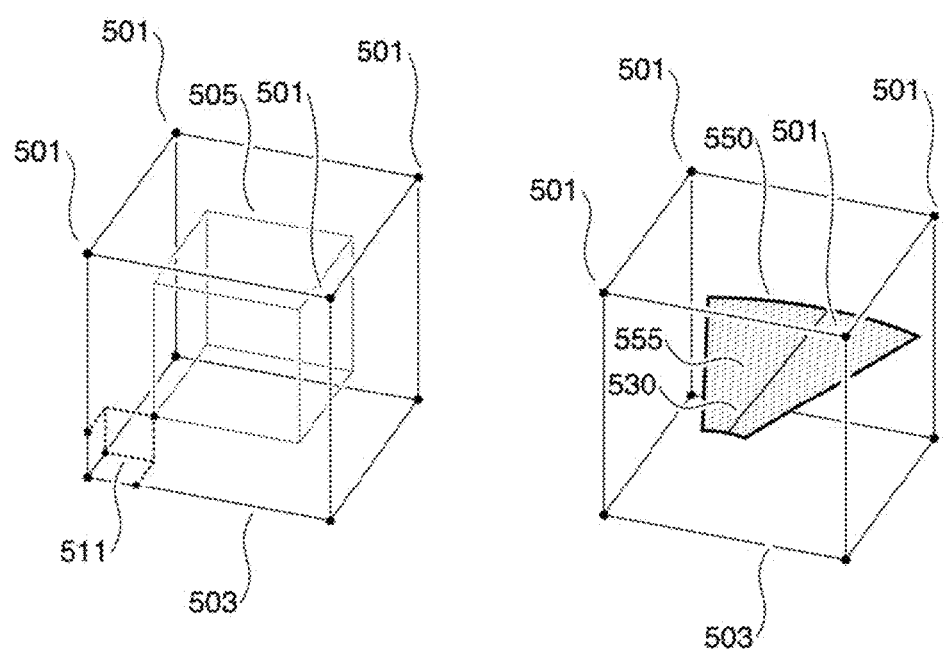
FIG. 5 schematically shows a geometric relation of an image-acquisition plane in a patient-fixed frame of reference, as shown to a field operator as a geometric form in a 3D display.

Since these various depth cues are sparse or lacking in the figure format used here, FIG. 5 presents the displayed view in a stylized fashion.

The 3D display shows the fiducial positions as markers 501, using a transformation T that rigidly maps (u, v, w) locations around the model patient to positions in the display coordinates (x, y, z), where typically x varies horizontally across the monitor, y varies vertically across it, and z increases in the direction away from the viewer. The markers 501 are shown optionally with (or as vertices of) a frame 503 (e.g., graphical) displayed to serve as an additional depth cue for their position and for the additional display elements described below. For clarity FIG. 5 shows four such fiducials in a square, and the frame 503 as a cube, but other geometrical choices for their number and layout will be apparent to those skilled in the art. The line 530 illustrates a typical path along which an ultrasound pulse travels and returns, giving rise to echo data: a system using a single such path is an 'A scan', whereas the assembly 550 of such lines is a 'B scan'.

Within this contextual display, and usually entirely within the frame 503, the computer shows a 'volume of interest' (also referred to herein as region of interest, often abbreviated VOI or ROI in literature) 505, corresponding via the transformation T to a volume V containing the region in the model which holds anatomical structures of clinical interest (or would hold them, if the model were anatomically complete. Additional graphical elements such as lines 511 relating the volume of interest 505 to the frame 503 may be included as further depth cues to the user. The computer determines the volume of interest 505 by code that refers to the positions of the fiducials (assumed to be in their standard anatomical locations), and estimates the positions of the structures of clinical interest. In a preferred embodiment the code makes deductions from the fiducials regarding the posture of the patient, the scale of the pregnancy (not identical to the developmental stage, since the size and even the number of equally developed babies may vary), and similar variable elements, using these date to sharpen these estimates and reduce the required size of V. In simple examples, V can be the convex hull of the fiducial points, or 'all points within a radius R of the centroid of the fiducials', or other such geometric specifications adapted to the typical anatomy, but in a preferred embodiment, the system and software can acquire the needed completeness of scan from an 'expert system' (a term with a defined meaning in the field of software and artificial intelligence). It can assess the necessary sweep, to ensure that the volume of interest has been scanned, from a warping algorithm that maps the volume in a standardized, stage of pregnancy-adjusted anatomy to that of the individual mother-to-be from obtaining the position of the fiducials placed on the external abdomen.

In the same 3-dimensional image, but drawn in FIG. 5 separately for reasons of clarity in a limited format (and drawn for depth clarity from an angle which may differ from the viewpoint actually used in computing the display), the computer displays a planar structure 550. This corresponds by the same transformation T to the region in the patient model for which the scanner (if currently active), held in the current position, gathers material data by echoes. In training use it need not be active, since the system is not training the operator to guide the scanner by display of the current scanned image: indeed, a 'dummy' scanner with only the tracker functionality could be used for training systems. Further embodiments may display a virtual or real anatomy previously acquired, but no current acquisition is necessary.

In a preferred embodiment, the 3D frame 503 is so arranged relative to the eyes of the trainee 403 that the transformation T involves very little rotation, so that the representation 550 of the acquisition region turns about approximately the same axis as the scanner unit in the trainee's hand: a similar arrangement applies to the active image creation configuration described below. This harmony between the rotations felt in the hand and the rotations seen in the display makes control substantially easier.

The training then includes learning to sweep the planar structure 550 smoothly so that it passes through every point of the volume of interest 505 with a speed and uniformity of scan consistent with acquiring images interpretable by skilled personnel, and which yields the desired metrics either from automated machine processing of the image, or by interaction with a human professional.

It is emphasized that no image needs to be acquired in training: the training module merely tests whether the volume of interest 505 is sufficiently covered, and gives feedback to the trainee on this test. This is enabled by the said input reported (FIG. 4, element 411) from the 6DOF tracker (henceforth, tracker) 450 to the computational device 413 in FIG. 4. Algorithms and software are used in computing the particular scan area available from the location and orientation information as well as the accelerometer information on the smoothness of the scan. In particular, there is no need to acquire any image adapted to a particular anatomical orientation (which with a fetus, could be very variable), since the information for a 3D reconstruction is present in the invention. The approach currently used in the art does require real time display of the images, plus the expertise to grasp them and to perceive in anatomical terms the current position of the acquisition shape S: gaining that expertise is a training bottleneck. The present invention makes the task, and training in the use of the system and methods, much easier.

To provide the information to the operator during training to ensure that the image is properly acquired, smoothness of scan can be assessed by numerical tests of the succession of positions reported by the device, requiring changes in location and orientation to lie within prescribed limits. The software does not perform the sweeping motion of the sensor, which is controlled by the hand of the field operator, but it can detect jerky or over-fast motion and call for a re-do. In an embodiment, this may be displayed as a clear jump in the scan region, by for example showing the separated consecutive positions 550, together with a suitable warning display.

Figure 6:
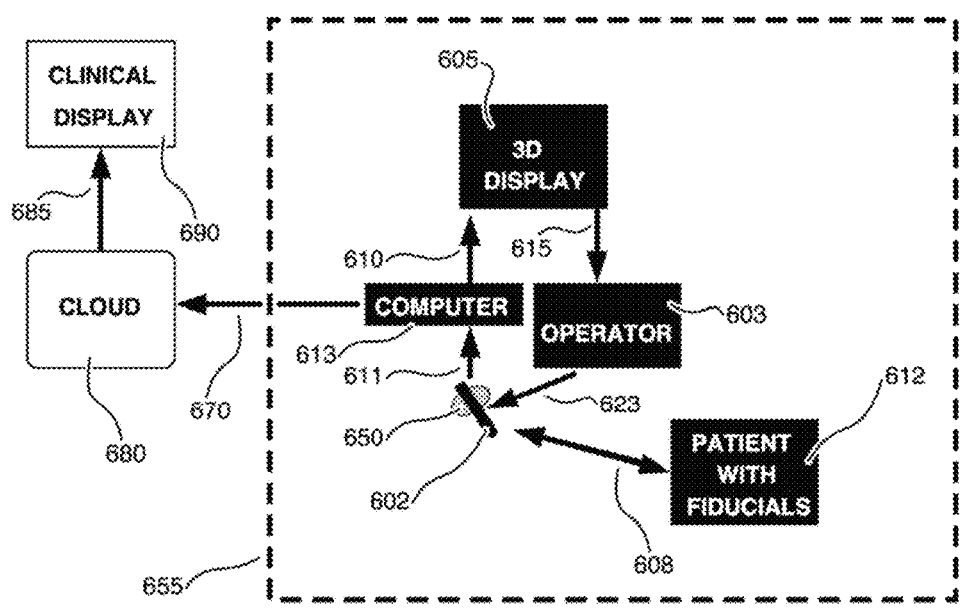
FIG. 6 schematically shows information flow in deployed use of the present invention, including connection with a separated clinical display, to which anatomical visualization may be reserved.

In active practice, after training, the model is replaced by a patient, and data are actively acquired by the scanner. FIG. 6 shows the information flow of an embodiment where the elements in the logical box 655 are the same as in FIG. 4. Thus all the numbers 402, 405, and so on are replaced by the corresponding numbers 602, 605 etc. which have the same meaning as the corresponding numbers in FIG. 4 except that the model 412 is replaced by a patient 612, and the trainee 603 is now an operator. There need still be no means for the operator to see the image data collected, though the system may optionally be capable of this, either in a separate display or mapped 610 as a texture onto the planar structure 550 within the 3D display 605, as seen 615 by the operator. (If this is done in the embodiment selected for practice, it can be anticipated in training by using a stored array of intensity levels I(i, j, k), perhaps from a library of several such arrays, without requiring the presence of real internal anatomy.) In a preferred embodiment these data are not displayed to the operator, but transmitted via the uplink 670 to a separate site 690, optionally via temporary or permanent storage in the cloud 680 and retransmission for delivery 685. At some point in this flow (the on-site computer 613, computing hardware in the cloud 680, or the clinical display site 690), the echo data and position data are reconstituted into a 3-dimensional array of intensity values, reflecting material properties at corresponding points in the volume V, as performed for example by the Freehand™ 3D system described in the Background above.

The construction of the 3D scan makes unnecessary the task of acquiring a 2D scan at a particular orientation, which is critical when using an ultrasound scanner 'live', or when viewing only individual images. A set of 2D scans from an untracked scanner (as used in current practice) may be useless in computing a fetal dimension metric like femur length, when one end of the femur appears in one scan, the other end in another, and the geometric relation between the scan positions is unknown. For such purposes, therefore, the user of an untracked scanner must select individually appropriate scans, whose quality can be judged only by inspecting the scans as they are made. The user of a tracked scanner, as described in the Background, is in current systems guided by the immediate display of the acquired planar image. The present practice thus absolutely requires anatomical awareness and judgment, and renders inevitable that the operator must see what is acquired. If the criterion is only fullness of sweep, with many orientations equally acceptable, the task becomes simpler, and training not merely becomes faster, but can be performed partially or completely with an automatic program, as in learning a video game without an expert tutor: this reduces the cost of the system, and removes a bottleneck to rollout.

At the site 690 a clinical user (who may be remote, and work in a controlled and licensed setting with institutional safeguards against breach of patient privacy, sex determination, or such other acts as may be forbidden by local law) can see the reconstructed 3D data, using means selected from the great variety of rendering and interface tools developed in recent decades. The anatomy can be rendered in 3D, making it easy to identify (for instance) the ends of the femur for calculation of its length. The commands available in OpenGL and similar frameworks make it simple to extract a planar slice in any position, and view it by a variety of user interfaces. Alternatively, or in combination with such display, smart software can extract such clinical parameters as femur length. In a preferred embodiment, with or without input by a clinician, the system assembles the data into a report listing such parameters and other indicators of the state of fetal health, which is returned via the cloud to the operator. If there is cause for action in the report, this fact is highlighted and the operator refers the patient to a local medical practitioner, to whom the report is digitally or manually made available. The local practitioner thus gets the benefit of an expert, or expert system, analysis of the patient's and fetus's condition, while no local person needs to see the ultrasound images. If the social and legal environment makes it appropriate, the reporting format may specifically exclude any way of specifying the sex of the fetus: moreover, the image data may be anonymized, so that a local person cannot successfully contact a person at the clinic with a request to know the sex of a particular fetus. The overt identity codes for patients, visible in the patients' locality, and the IDs under which the image data are presented and analyzed, exist in a hashed correspondence like that of usernames and passwords. Many ways of structuring such security will be apparent to those skilled in the art.

Certain environments, as mentioned above in the Background, may mandate not merely the local non-display of the images, but a guarantee that they remain inaccessible. The echoes received by the scanner do not in themselves constitute images: they require substantial processing to produce an Intensity (i,j) array of the kind that can be displayed as pixels on a display device. It is therefore useful to examine the flow of this processing (FIG. 7).

For clarity we show ultrasound emission 711 and the conversion by the transducer 712 of received ultrasound to analog electrical signals as separate functions, though typically they are handled by the same hardware. The emitter 711 creates emitted pulses 707 of ultrasound which travel to the region of the patient 700 to be scanned, along paths such as the straight line 530. Reflecting from structures 701, the echoed sound 708 of these pulses travel to the transducer, from which analog signals 715 travel to an analog-to-digital converter 720, and from there as digital signal 725 is sent to the echo identifier 730 which identifies echoes and their time of flight. To do this the echo identifier 730 absolutely requires transmission timing data 721, which give the times of emission, to travel from the emitter 711. The travel times cannot be estimated without this. For an intrusive device to capture sufficient data in any stage up to the echo identifier 730, therefore, it must capture them at multiple points. A device which reads the emissions and echoes, distinguishing them from each other and ambient noise, then computes for itself the echo times, would require much more engineering effort than making a stand-alone ultrasound scanner (or buying an illegally trafficked one), with errors added by noise and mis-estimation, and would legally constitute a scanner with the present system as ultrasound source, so it is barred both by law and practicality. It offers no advantages over an ordinary scanner, because it would show only degraded versions of the individual 2D scans: without the 3D reconstruction function enabled by 6DOF tracking data, only anatomical expertise can offer the guidance necessary to acquire useful scans.

Electronically capturing both the transmission timing data 721 and the transmission of the captured echo analog signal 715 or as digital signal 725 would require invasive electronic hacking at the hardware level, with no simple points of access if the functions involved are communicating within a single integrated chip.

As an additional security option, the digital communications 719, 721 and 725 can be encrypted within the handheld sensor unit itself, using encryption hardware included within the device and a key specific to each individual device, so that capturing the binary data alone has no value. Many means of encryption will be evident to those skilled in the art: without limiting intent, we observe that these include the encryption of data from the emitter 711 relating times at which pulses were emitted to the directions of these pulses (without which the line 530 along which an echo returned cannot be known), making interception of the transmission timing data 721 valueless; the returned signals in the form created by the analog-to-digital converter 720 may be encrypted, making interception of the digital signals 725 valueless (for this method, as with the time/direction data from the emitter 711, the echo identifier 730 must be equipped for decryption); the data from the position sensor 717 may be encrypted, preventing its use in constructing a 3-dimensional image from the 2-dimensional scans of successive polygonal regions 555; the association between lines 530 and the echo patterns along them, analyzed by the echo identifier 730, may be encrypted, preventing their use in constructing even a 2-dimensional image; and so on. By moving any decryption step outside the process 766 performed locally, an embodiment can prevent the existence of detectable images within the local system, where human security (against bribery or other forms of persuasion) may be weak.

If the time-stamping of emissions from 711, the digitization by the analog-to-digital converter 720 of returned signals, and the echo identification by the echo identifier 730 are all performed within a single chip, there is no vulnerability of the scans up to the point of the echo analysis by the echo identifier 730. The data flow 735 from the identification of echo flight times and directions to the creation 740 of an array of pixels need not pass along a distinct, hackable communication pathway between physical components, as it is most efficient to use each evaluated echo within a single chip to modify one or more pixel values in the image array, then discard it from memory, rather than store or communicate the whole set of such echoes along lines 530. Access to data that a microchip does not send to its communication ports is practical only in a large and extremely costly 'clean room' laboratory setting, with microscopic equipment. This does not guarantee that it will not occur, but it is evidently not cost-effective for the criminal. Moreover, if the legal clinical display 760 is at a remote site, the unit is necessarily registered with a larger ecosystem that transmits 755 data and reports, manages and encrypts records, etc., and should include regular inspection of remote equipment. It is straightforward to mandate, if legally required, that such inspection does take place and includes alertness to evidence of hacking at the hardware level.

Hacking at the software level, which need not leave physical evidence, can thus only occur once reconstruction processing has created a pixel array, or equivalent data. It may be required that we guarantee the impossibility of access to these data.

If reconstruction processing is deferred to the cloud 750, no image actually exists within the local flow 766, so that access requires the addition of local processing. Unless the software is locally programmable, the hacker must add hardware, which will be easily detected in the inspection suggested above. There is no need in a mature production device (as distinct from experimental prototypes) for local programmability, so the code can be unchangeably 'burned in' to the embedded chips. This thus represents a high level of security against local access to images.

If the data size of unprocessed digital 'time and echo' data is significantly larger than that of the reconstructing images, however, this deferral may not be optimal. It can coexist with relatively low bandwidth, since the system does not require real time upload 745 to the cloud 680 or, as in this Figure, 750, (data can queue up to be sent over seconds or minutes, if there is local memory to wait in), but it implies a significant cost both in total packets transmitted and in turn-around time before a patient receives a report. In this case the algorithm used to create the image array can be combined with a strong encryption algorithm, of a kind well known to those skilled in the art, using a key that is specific to the particular unit and registered with the overall system in the cloud 750. In this case the image does exist locally, but never as a whole in unencrypted form. Usable access to it would require not only physical access to the image at some point where it is stored or transmitted, but decryption of a level that uses special equipment and expertise available only to large governmental and other organizations is easily available and known to those skilled in the art. Further, transmission via the web to the cloud can use a protocol such as HTTPS (technically, the result of simply layering the Hypertext Transfer Protocol (HTTP) on top of the SSL/TLS protocol, thus adding security capabilities to standard HTTP communications) widely used for secure commercial transactions. Similar encryption may be applied to the communication 722 of the tracking data for the locations and rotations of the emitter 711 and transducer 712, which makes possible the reconstruction in the cloud 750 of a 3-dimensional data array to be visualized in the interactive display 760, and is hence essential to the avoidance of a need to produce individually useful, anatomically guided planar images. Without these data, and reconstruction software that uses them to turn a freehand series of slices into a volume data set that can be sliced in new directions, the user of a hacked instance of the present invention requires the same level of anatomical expertise as the user of an untracked scanner obtained on the black market.

By these or other arrangements that will be apparent to those skilled in the art, it is clear that images can be made inaccessible to the local user with a level of security adequate for presenting misuse.

In the context of legal prohibitions it will be necessary to consider the working of the system in the light of the exact phrasing of the law in each relevant country: the working may be slightly adjusted to harmonize with the law, or (in light of the evident social value of making the medical benefits of ultrasound available without sex determination) the government may be persuaded to adjust the relevant Acts or regulations.

To the best of our current knowledge, the use of 3D graphical display to guide the user's creation of the series through a geometrically displayed target volume is new, for either training or active use. Its importance here is to fully separate (as Freehand™ 3D does not) the selection of separate viewing-slice selection from the reconstructed 3D dataset (as well as volume rendering, recognition of the whole femur by smart software, etc.) from anatomical guidance of the original slice acquisition, both making useful a series that was not guided by anatomical awareness to create individually significant slices, removing the anatomy-based element of the required skill and training in acquisition, and creating the potential for remote medical viewing of images that need not locally be visible, or even (in the chosen slice position) exist. Although 3D reconstruction from hand-guided planar slices is not in itself a novelty, it is a further advantage of the present invention, that the reconstruction software need not even require additional computing power locally (in the device or an attached computer) since it can run on a server in the cloud, shared between many such devices. An embodiment may perform the computation either locally or in the cloud, depending on the trade-off between the cost of local computing power (which for decades has dropped according to Moore's Law) and the cost of communication bandwidth. In either case, the availability of 3D images for algorithmic quantification of diagnostic measures permits improved diagnostic value without the requirement for more costly 3D-specific hardware such as a parallel beam device.

Recapitulating, an aspect of method technology in the practice of the present technology includes a method of acquiring medical images, in which: a) an on-site operator manually operates a non-invasive sensing device to acquire echo data from points at computable distances and directions from the device, interior to a chosen region of a subject (e.g., at internal body locations where organs or tissue growth occurs, including a fetus or tumor); b) identifying fiducials placed at anatomically defined exterior points of the subject; c) determining the locations of the fiducials in the reference frame of a position-determining subsystem; d) establishing a correspondence between space physically occupied by the fiducials and numerical space in which the chosen region is specified; e) monitoring the position and orientation of the sensing device at the time of each acquisition of a set of echo data; f) optionally preventing local access to such echo in any form which would allow local reconstruction of an image; g) displaying by computer on a visual display device a combined representation of the positions of the fiducials or of a reference anatomy model located in reference to them, of the chosen region, of each successive current location concerning which the sensor can obtain echo data (in a preferred embodiment, without the echo data themselves), with the sensor in a current position reported by the position and orientation monitoring sub-system; h) the computer determining which sub-regions of the chosen region have not yet been sensed in levels of detail and of quality that satisfy pre-determined quantitative image criteria, in respect of the acquired data; i) the computer displaying the said sub-regions to the operator, showing the sub-regions in relation to the displayed representation of the fiducials; j) assembly in a computer of the acquired data into a three-dimensional image data array; and k) using the three-dimensional image data array to display an image to a user who need not be at or near the location where the patient is scanned.

A further aspect of the present technology is the system enabled and constructed to perform the methods, such as a system for acquiring and transmitting medical images, having:

a) a manually operable, non-invasive sensing device capable of acquiring echo data from points in an interior region of an animal subject at computable distances and directions from the non-invasive sensing device;

b) fiducials (markings that are at least one or both of visually observable or mechanically observable) at anatomically defined exterior points of the animal subject;

c) a computer configured to determine locations of the fiducials in a reference frame of a position-determining subsystem;

d) the computer, in communication with the non-invasive sensing device, being configured to establish a correspondence between space physically occupied by the fiducials and numerical space in which the interior region exists;

e) the computer configured to determine and to monitor from received signals containing echo data, position and orientation of the sensing device at a time of acquisition of each data point within a set of point data;

f) a visual display device in data communication with the computer, the visual display device configured to provide an image of a combined representation of positions within the region of the fiducials or of a reference anatomy model located in reference to the fiducials, of each successive current location concerning which the sensor can obtain echo data, with the sensor in a current position according to the position sensing sub-system;

g) the computer configured to execute code to determine which sub-regions of the interior region have not yet been sensed in levels of detail sufficient to meet predetermined standards of image quality within the acquired data;

h) the computer configured to prevent local access to echo or image data, optionally including hardware encryption;

i) the computer configured to transmit image data from the acquired data to display the sub-regions to the operator on the visual display device, displayed images showing the sub-regions in relation to representation of the fiducials;

j) a computer configured to assemble the acquired data into a 3-dimensional image data array; and k) connection to a system for display of such 3-dimensional image data.

It is an aspect of the technology of the invention that the display presents the operator with a three-dimensional view. For purposes of clarity, 'three-dimensional' is a term with broader meaning than a common interpretation as 'stereographic' which refers to presenting the viewer's two eyes with two distinct views, from which triangulation in the viewer's visual cortex can deduce distance. (There are many ways to achieve such a presentation, including but not limited to the wearing of glasses with different color or polarization filters or display-synchronized shutters for the two eyes, the use of prisms to give two displays the same apparent position, the placing of different views directly in front of the eyes with lenses to adjust focus, holography, Pepper's ghost displays and other technologies familiar to those skilled in the art. All may be used within the spirit of the present invention.) Popular usage of '3D' tends to refer narrowly to stereography, but for present purpose '3D' or 'three-dimensional' display refers to any display in which there are depth cues that can be visually or automatically interpreted as having width, height and depth. Using FIG. 5 as itself an example of depth cues, the overall frame 503 which is recognizable to a viewer as a rectangular box, having width across the figure, length vertically in the figure, and depth 'into' the figure, despite being in itself a two-dimensional pattern of dark points against white ones. This is achieved in this instance by a representation of occlusion by the breaking of lines that are to be perceived as passing behind other lines, as in the breaking of all lines that pass behind the edge 504 of the frame 503. (With wider objects in differing colors, this graphical device of a visible break in the occluded element is not needed.) Such cues may include but are not limited to occlusion (illustrated by the way parts of the frame 503 pass in front of the polygon 555), perspective, and parallax: the way that an eye's view changes with the eye's motion. This cue may be included in the present system either by an eye-tracking camera and software (increasingly available as a commodity item) or by other means (e.g., automatic tracking through software or manual response to software indicators) of tracking head position. Since the proposed system already includes tracking hardware able to continuously report the location of the scanning device 202, and such hardware can often follow more than one object (for example, the FASTRAK® hardware and embedded software system sold by Polhemus tracks up to four sensors), inclusion of head tracking for parallax is a natural though not essential variant of the proposed system. Other cues to precise 3D location include the addition of graphical elements such as the lines 511 (without which a single-eye view like that in FIG. 1 does not show directly how close the region of interest box 505 is to the near side and top of the frame 503), such as rendering with shadows cast by one structure on another, and such as others well known to those skilled in the art. Any one or more of these may be used in the spirit of the present invention to qualify the display as 'three-dimensional'.

This invention discloses various additions to the display and data reconstruction previously disclosed. We refer below to the region 112 acquired, by the same identifier, even when the sensor is used as part of a system arranged differently to FIG. 1. Recall that the system, by containing anatomical information, can predict with reasonable accuracy the location of internal organs such as the uterus, heart or gall bladder. These points are referred to as 'fiducial points', or more briefly 'fiducials.' Their positions may be identified automatically by the system itself, from a visual inspection comparable to the operator's view of the subject, but in our preferred implementation the operator places small physical objects stably on the subject's skin, at the fiducial points. (By a common elision, these liducial objects' are also referred to as 'fiducials.') The positions of these objects, in the coordinate frame of the position-reporting device, may be established by the tracking hardware and software system acting without human input, for example by inclusion in the objects of position sensors such as the multiple sensors supported by the FASTRAK® system, or of visual features making them easily located by a camera-based system, or of other such factors appropriate to the tracking system. However, in one preferred implementation the fiducial objects are simple passive items, which the operator may touch in turn using the tracked sensor. This is discussed in more detail below, with reference to FIG. 11.

Data most directly obtained by an ultrasound device are not point-by-point images (such as the collection of numerical pixel values obtained and stored by a digital camera, or the brightness at different points in an X-ray film, resulting from chemical changes triggered by arriving photons), but rather are echo records. An emitted ultrasound pulse in a particular direction (comparable to an optical ray line, arriving at one pixel and modifying that pixel's brightness and color) is echoed by sound-reflecting matter at different distances, with the echoes received at correspondingly different times. The use of a single direction, with a plot of echo intensity against time, is known as 'A-scan' ultrasound. It is useful (for example) in measuring the distance between the retina and lens of the eye, but the plot is not an image of the eye. An image of the eye along that line would consist of a line with varying brightness B, proportional to echo strength. For a single line the plot view is clearer, but for a fan distribution of lines in varying directions, this 'B-scan' mode gives a useful display, combining to give a planar view of a slice through the eye or other tissue. This is the most common sonogram display in current use. For the purposes of the present invention it is significant that the echo data only become pictorial by means of a non-trivial computation, essentially 'the echo along line L (such as the line 530 in FIG. 5: the polygon 555 is a fan-shaped collection of such lines) has intensity I at time T, which corresponds by the speed of sound c to reflection at a point T/2c along L, passing near the space point we represent by pixel P, whose brightness we increase by I, more strongly if the passage is nearer'. In current art this computation is performed in real time and the resulting set of pixel brightnesses shown on a 2D display, but these values are not the ultrasound data themselves. Moreover, if the direction of the line L is unknown, image creation is impossible. In particular, if the direction is unknown to a person or system with access to the data, due to encryption of data specifying it, that person or system cannot construct the image. In the present invention, it is not necessary to provide the operator, or any local person or system, with the coordinated system of directions, times and echo strengths that make image reconstruction possible. This permits an important enhancement of security in embodiments of the invention where image access is denied to the operator, since locally no image even exists for unauthorized access: the image-creation computation can be performed elsewhere, and the created image data made available only to distant authorized clinicians, who examine them in 3D or by slices chosen independently of the original positions of the hand-held sensor. A report of predefined informational content is returned to the patient site, optionally including images selected by the clinician, which can exclude proscribed information such as sexual anatomy.

In a first method of additional guidance, the internal structure of the patient (represented by a line hatching pattern in the subject 801) is scanned 802 by the operator 803 in the region 812 and the resulting image is shown not as a polygon 810 in a fixed display 805, as in current practice, but as a texture polygon 555 mapped to the polygon 550 which moves within the frame 503. This variant does not conceal anatomical detail from the operator, and would not therefore be appropriate in markets where sex-selective feticide is a problem, but it does assist the operator in relating hand position to anatomy, and can therefore in other markets offer better cognitive ergonomics. In some scanner positions the angle of view of the polygon 550 may be too oblique for clarity, but there is no bar in this variant to a separate display polygon 810 in a fixed display box 805, 806 of the usual kind, in a separate display device 813 to which the probe is connected via a link 811 which may be wireless or in a shared window.

Figure 9:
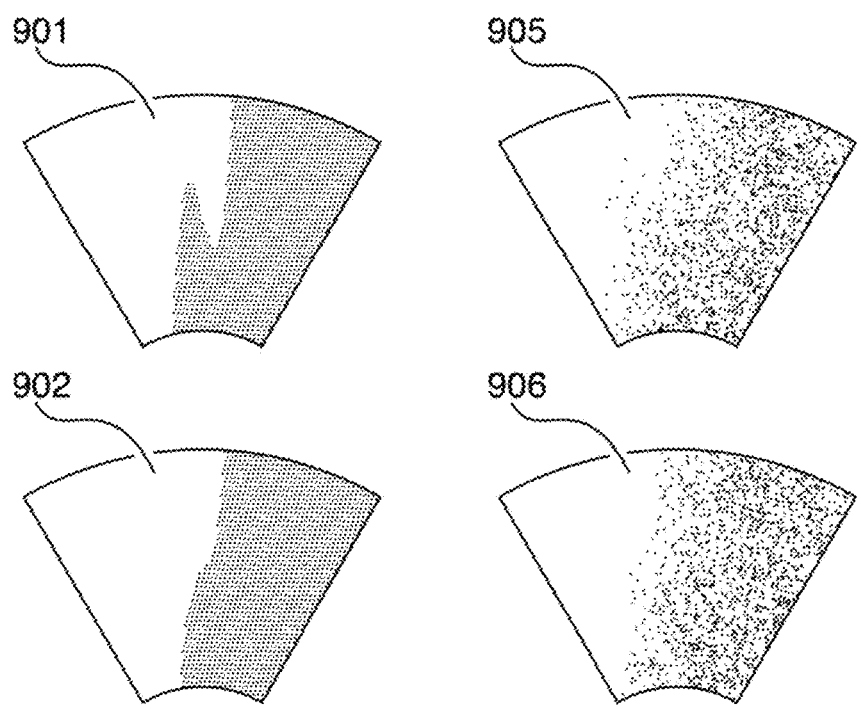
FIG. 9 schematically shows patterns in the acquisition region of a sensor, and blurred versions of those patterns.

In a second method of additional guidance, the currently acquired image is displayed in the same real-time way as a texture on the polygon 550, in the same apparent location, but it is blurred throughout. For illustration within the conventions of patent Figures, we represent the image data as a pattern of dots such as 901 or 902 in FIG. 9. (Current technology uses shading, in gray levels and sometimes, to represent additional data such as Doppler values describing motion, in color.) If the scanning device and processing is sufficiently precise, considerable anatomical detail can be seen, represented here by the contrast between the patterns 901 and 902. Since this detail can include the sex of a fetus, we may wish to suppress it from local displays. Without the computational difficulty of identifying anatomy, we may simply modify the local display by for example convolving the image with a Gaussian: this is represented in FIG. 9 by randomly moving the individual dots in the patterns 901 and 902 to create the patterns 905 and 906 respectively. (Blurring may be done by such displacement of small elements, or by pyramidal blurring, or by convolution with a Gaussian kernel, or by the fast method discussed in Quasi-Convolution Pyramidal Blurring by M Kraus in the Journal of Virtual Reality and Broadcasting: 6 (2009), or by many other means well known to those skilled in the art.) The result is that large features such as the dark and light areas in the patterns 901 and 902 remain visible, but the fine differences are no longer apparent. In a fetal scan the wall of the uterus could remain blurrily visible, as would the location of the fetus, but fetal details such as the genitalia would not. Blur would diminish the diagnostic value of the image, but the operator is not responsible for diagnosis. It applies only to the local display, while image data with all available clarity are transmitted to the remote clinical center.

We expect the visibility of large scale features even in a blurred view to enhance the operator's skill and confidence in moving the scanner appropriately, particularly when they repeatedly appear in a particular three-dimensional location in the frame 503, assisting the operator in creating a three-dimensional mental map of the subject's anatomy.

Such blurring may also be used with a traditional ultrasound display (FIG. 1), showing the blurred image in a planar image 106, in combination with transmission of the un-blurred data to a remote location, as disclosed in our previous application. However, our preferred implementation remains a three-dimensional geometric display, where hand-eye coordination makes it easier to judge the spatial location of the large-scale anatomical features which remain apparent through the blurring.

In a third method of additional guidance, the system finds edges in the image data, by means familiar to those skilled in the art. (See, for example, *A Survey on Edge Detection Methods*, Technical Report: School of Comp. Sci. & Elec. Eng., University of Essex: CES-506, M A Oskoei & H Hu, 2010, or *A Survey on Edge Detection Using Different Techniques*, K Kaur & S Malhotra, Int. J. of Application or Innovation in Eng. & Management 2:4, April 2013).

Commonly such means involve a first stage of detecting 'edge-like' points by some measure of local contrast, including but not limited to the use of operators such as a Sobel, Prewitt, Roberts, or Laplacian. Often many non-edge points appear edge-like due to noise, or edge-points fail detection due to local blur, so a second stage uses the detection data to construct substantial edge curves. This may be done by finding chains of edge points and discarding small fragments, but it is often more effective to use active contours (pioneered in *Snakes: Active contour models*, M Kass, A Witkin, D Terzopoulos, Int. J. Comp. Vision 1:4), 321-331, 1988), which numerically move around and fit themselves to as high a total of edge intensity as possible, while resisting sharp bends. This resistance may conceal detail, which for some applications is undesirable, but for the purposes of the present invention is a benefit, as is the reconstruction of a smooth edge from noisy image data.

Figure 8:
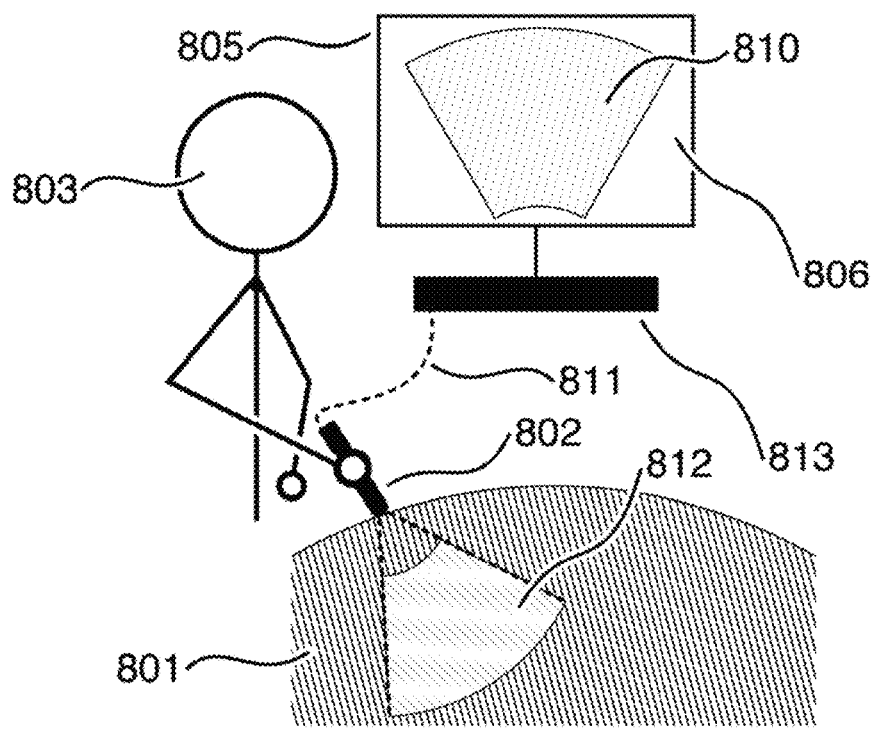
FIG. 8 schematically shows the relation between a pattern in the acquisition region of a sensor, and the current way to display that pattern.
Figure 10:
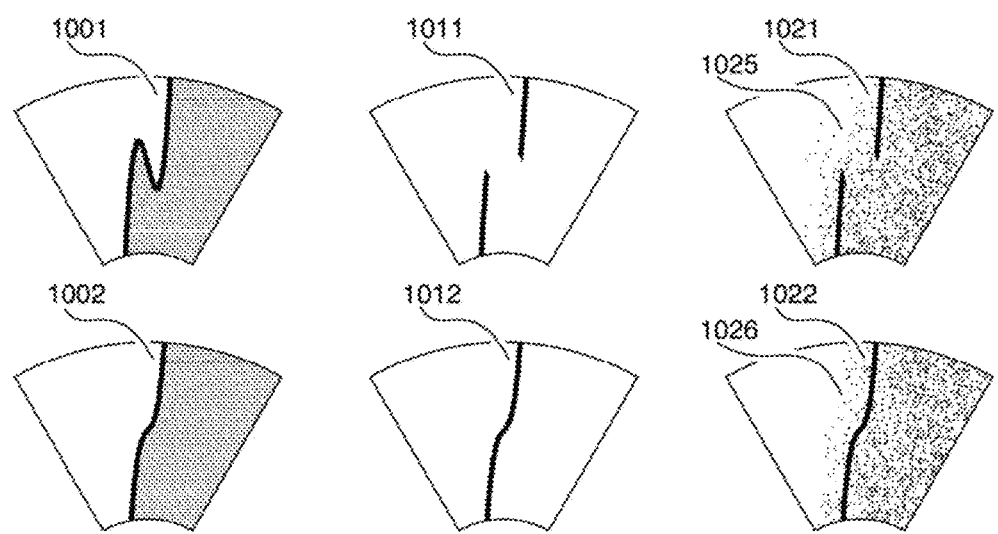
FIG. 10 schematically shows edge curves extracted from the patterns in FIG. 9, simplifications of those curves, and their superposition on the blurred versions in FIG. 10.

By the above means, or by other edge-finding means familiar to those skilled in the art, we fit edge curves to the image acquired by the scanner. This is illustrated in FIG. 10 by curves 1001 and 1002 fitted to the patterns 901 and 902 respectively. In the present invention we limit display of these curves to long, low-curvature segments of them, as in the curves 1011 and 1012, which we show on the moving polygon 555 or the fixed display 805, or both. For a segment to be displayed, it must pass both a 'length test', such as restricting display of image content having a length only in excess of 4 cm (a high upper bound for the penis length of a full term fetus), and a 'curvature test' that the radius of curvature must nowhere be less than a predetermined value such as 1 cm to allow display of the image content. These limitations render nearly impossible the revelation of fine detail such as genitalia, while providing strong cues as to anatomical location of the region 112 that is scanned. As with blurring, these partial edges may also be shown in a traditional ultrasound display (FIG. 8), showing them in a static polygon 810, in combination with transmission of the image data to a remote location. However, our preferred implementation remains a three-dimensional geometric display, where hand-eye coordination makes it easier to judge the spatial location of large-scale anatomical features.

Beside echo density, many other features may be extracted and displayed for guidance, such as a sinus or similar cavity, within the spirit of the present invention.

In a fourth method of additional guidance, a preliminary analysis of the echo data locates points whose sound reflections are sufficiently strong, relative to the other echoes currently received, to imply that these points are occupied by bone or a calculus such as a kidney stone or gallstone. These points are added to the display, either within the current polygon 550 or 810, or cumulatively within the three-dimensional view, without revealing fetal sex but assisting the operator in anatomical judgment of the scanning location (whether fetal or otherwise). If the scan has a particular anatomical target within a fetus or targeted organ, and the operator has enough anatomical expertise to recognize from the skeletal cue that this target has already been imaged, the operator may terminate the scan before the system reports that the target box is completely filled. Conversely, if the quality of the skeletal view appears poor in a particular sub-region, the operator may rescan that sub-region more carefully, indicating to the system that the new data are to be emphasized over those acquired earlier.

In a fifth method of additional guidance, features such as those just described are displayed 1021 or 1022 in superposition on the blurred image 1025 or 1026 created as described in the second method above.

In a sixth method of additional guidance, numerical measures of clarity are applied to the image data. These may include, but are not limited to, the localization of high values of edge-likeness measures, as discussed above; the value of entropy computed for the values assigned in small connected regions; the degree of correlation between values nearby in the image, as against values more separated; and other such measures as will be evident to persons skilled in the art, within the spirit of the present invention. If high edge-likeness values occur for spatially large regions, if entropy values are above an appropriately chosen threshold, if correlation values are below a threshold, etc., it is clear without human visual examination that the image is insufficiently clear, and the image fails a 'local clarity test'. Where an image passes these tests, we may apply such 'local resolution tests' as subsampling, supersampling the result, and assessing the amount of change. If this change is small, the local resolution of the image is effectively that of the subsampled (coarser version), which in the presence of values differing by more than a threshold amount indicates a level of resolution inadequate for the discovery of clinically important detail.

Another measure of quality relates to the fact that the acquisition region may be moving 550 may be moving slowly in the direction normal to itself, producing closely spaced planes of acquired data, but moving fast in a lateral direction, with resulting motion blur. This may be detected by computing anisotropy measures of the correlation between neighboring data slices, with levels above a threshold failing the corresponding 'transversality test.'

We refer to tests of clarity, of resolution and of transversality collectively as 'local quality tests'. Also included in this term is a straightforward test for gaps: if for a particular point in the target region, no image data have been registered for any location within a predetermined radius of that point, the point fails a 'gap test'. Other such tests may be added, within the spirit of the present invention. In particular, the construction of such tests for Doppler data (reporting a component of velocity radial to the current position of the sensor) will be evident to those skilled in the art.

We display in the frame 503 the region of such unsatisfactory points within the polyhedral volume of interest 505 as a translucent blob, as a cloud of opaque points, or as such other visible indication within the capability of the available graphics processor as most clearly gives the operator a sense of the spatial location of this region, and signal the requirement for repeat scanning of this region. Each type of failure is associated with particular causes, such as: a low value of resolution indicates that the user is moving the sensor too fast; a too-wide separation of acquired data planes indicates a motion too fast of the acquisition region 550 in the direction normal to itself; failure of a transversality test indicates a motion too fast of the acquisition region 550 in the direction tangent to itself; a high level of entropy indicates jitter in the sensor location and/or orientation; and so forth. These may be confirmed by analysis of the series of recorded locations and orientations of the sensor. Corresponding to each of these problem modes is an improvement that the user should make, when re-acquiring data for the problem region: respectively, these may be summarized as the suggestions "move more slowly", "turn the acquisition plane more slowly", "turn the acquisition plane more normally", and "move more smoothly". (Since recorded motion can be analyzed without reference to the acquired image data, similar messages can be included in a training schema for the system, without any images being acquired or processed. Users can thus become well practiced in the required style of movement in an inexpensive imaging-free version of the system, omitting the image sensor and processing equipment, and sensing only positions and locations.) We refer to such messages to the user as 'feedback hints'.

When the operator has completed this task, and achieved adequate quality in the region of previously unsatisfactory points, the resulting data are three-dimensionally integrated with the others acquired in this session, in creating a diagnostic data set for the remote clinician.

In a seventh method of additional guidance, numerical measures are applied to the acquired image data, revealing whether their planes are sufficiently closely spaced for the reconstruction of a volume data set. If they are not, the region within the volume of interest 505 where better data are needed can be three-dimensionally marked (by a smaller box, or by other graphical means familiar to those skilled in the art) as requiring a repeat visit to the region 112 by the scanner.

In an eighth method of additional guidance, the ultrasound system is capable of Doppler analysis, for example giving indications of maternal and fetal blood flow by frequency changes in the echo. Such analysis is subject to problems such as aliasing, where the low pulse repetition frequencies more sensitive to low flows/velocities result in interference effects with periodic motion in the scanned tissue. Moreover, it is of the nature of Doppler analysis that it reveals only the component of target velocity toward or away from the emitter-sensor unit, not across that direction. To assess blood flow along an artery, using a single scan view, the sensor must be 'looking along' the artery, rather than seeing the artery from a sideways direction. (This language is appropriately vague, since the sensor does not need to be precisely in line with the artery. That case gives the strongest signal, but an angle of 30° between the viewing direction and the artery direction reduces the reported component by less than one seventh. Even an angle of 60° reduces it only by half.) In a use like obstetric examination, where the fetus may rotate unpredictably, the best direction cannot be known in advance.

In current practice, an experienced operator alters the scanning approach to obtain good insonation angles so as to achieve unambiguous flow images, as judged by immediate viewing. In the system here disclosed, the operator does not have a real-time view of the flow image, by which to adjust for good quality. Consequently, just as for static anatomical use we replace the acquisition of individually revealing 2D images by the acquisition of intensity data for a 3D region (later resampled in arbitrary planes, or volume rendered, or otherwise displayed independently of the original sensor positions), we acquire 3-component vector data for a 3D region. One 3D scan of the kind previously described gives one flow-velocity component at each point, the component in the direction from the sensor. We thus require at least three such scans, so arranged that the three ultrasonic 'rays' passing through each point do so in mutually transverse directions, rather than coplanar or collinear (or within a limit of, for example, 45° from these degenerate cases). This may be achieved by the operator moving the sensor around three non-overlapping zones of the body surface, while aiming it at the same internal region of interest, or by other motion protocols that will be evident to those skilled in the art. As an alternative, sensors may be mounted on a separating frame and directed toward a common three-dimensional region. This involves less operator time (and a lower probability of target movement complicating the process) but more hardware and more operator skill, and is not our preferred first embodiment.

For each point p, the system computes a best-fit single vector for the 3-dimensional flow vector v at that point, from the three or more separate echoes recorded from that point. (Note that the field of vectors v is in our preferred first implementation not displayed to the operator, as this would also reveal anatomy, but only to a remote clinician. However, it may be displayed to the operator in an implementation for strictly local use, and its 3-dimensional character has advantages over the current art, for such use.) To a considerable extent the use of echoes from multiple directions can reduce the impact of interference effects and other artifacts common in a single-direction scan, but where the best fit v fails to come within an appropriate criterion of matching the echoes actually observed, we mark p as a 'bad point'.

In a preferred implementation of the above eighth method, the system does not merely detect that the Doppler data are inadequate, requesting a repeat, but derives a probable angle of attack for the scanner at which better results could be achieved, and gives an indication of this such as a visible three-dimensional arrow (or analogous indicator of position and direction, as will be evident to one skilled in the art), within the frame 503, to assist in achieving a better result.

A ninth method of improved acquisition of an integrated 3D scan allows for movement of the target during the scan, such as that of a fetus. A best fit description of the motion during the scan of identifiably rigid elements such as fetal bones allows the creation of an overall 4-dimensional velocity field, with a motion vector at points (x, y, z, t) representing position (x, y, z) and time t within the scan. By integrating this to give motion curves, echoes from a point (x, y, z, t) can be referred back to the spatial location of the same anatomical point at a fixed reference time $t_0$. This computation is performed before presenting the final 3-dimensional scan to the clinician, with removed or reduced artifacts of the motion.

A tenth method of improved acquisition of an integrated 3D scan allows for regular, repeated movement during the scan of the target, such as the beating of the heat. This motion is unavoidable, but periodic rather than unpredictable. It repeats fairly accurately (in calm conditions) at intervals of T=(one minute)/(current heart rate), typically less than a second. Collecting the scan data together with time stamps and the output of at least one electrocardiogram or other pulse-related sensor, and assuming regularity of the motion, we collect echo data for a sufficient density of points (x, y, z, r), where (x, y, z) represents spatial position and r is cardiac phase: the fraction of T elapsed since (say) the closure of the atrioventricular valve. The acquired image is thus 4-dimensional (giving either scalar echo strengths or vector flow data), and the repetitive nature of heart motion means that gaps can be revisited. In an exemplary illustration of the guidance provided in this case, the display may show a square descending at a convenient speed through the region in which the heart is located, leaving the top of the region at a time when r=0. The operator is required to move the sensor so that the geometric display of the location of the data acquisition plane moves with this square: it is not necessary to reach the bottom of the region at the same phase as it left the top. When this motion has been achieved with sufficient accuracy, a square moves down with the same speed but beginning at a time (for example) one-tenth of a period later, with $\tau=T/10$. This is followed by a motion beginning with $\tau=2T/10=T/5$, and so on for ten motions altogether. By this means, combining the capabilities of a human operator and consumer-level electronics, a basic planar sensor becomes a scanner which can support quantitative estimates of such diagnostically valuable indicators as ejection fraction.

Once the three dimensional image data set has been constructed from the collection of multiple echo data points, the final set of three dimensional image data can be used in a number of different fields of technology. The image data may be used to indicate a need for surgical or medication treatment. They may be used to numerically determine the shapes of scanned structures, such as a femur or heart, and derive therefrom measures of clinical importance (see for example the paper "Segmentation of Speckle-Reduced 3D Medical Ultrasound Images" by P C Pedersen, J D Quartararo and TL Szabo, 2008 IEEE International Ultrasonics Symposium Proceedings, pp 361-366, and references therein, for relevant art). The 3D image data may be used to determine the quantity of medication to be delivered, and be used to determine the point of delivery (e.g., by catheter or by hypodermic needle). The 3D image data may be used to define regions for specific surgical plans (including direction of access to the subject of the image data, e.g., a fetus), enable the data to be exported to a three dimensional printing device to create models of the subject of the image (e.g., model of the fetus or the baby, physical models of the bone structure of conjoined twins, model of the organ structure within the patient), replication of organ images for evaluation by surgeons, use of the organ structure model for training of surgeons or practice of procedures, production of a holographic image from the three dimensional image, and other material manipulations using the three dimensional image data. These extended processes are known in the art and the apparatus used to convert three dimensional data into a substantive product such as an image, plan or physical structure is commercially available. These known technologies are intended to be used with the commercially available apparatus and methods, in the framework of the present invention.

In an eleventh extension of the earlier disclosure, the three-dimensional image reconstructed is used for the automatic analysis of anatomical structures such as a growing femur, including quantitative comparison with growth norms, objective sex identification to be non-erasably stored (permitting correlation of a clinical institution's records with later abortions, to raise statistical warning of security leaks), identification of structurally important features, and for certain conditions (such as identification of conjoined twins, mis-positioning of a fetus within the womb, or inappropriate arterial connections in an adult or immature body) identifying plans of treatment.

We now describe in a solely and non-limiting exemplary manner a procedural flow of the use of this invention, with the understanding that variants will be evident to those skilled in the art.

In a representative embodiment, the operator of the sensor is separated by distance (hundreds of miles, or a few miles of city traffic) or institutionally (separate parts of a hospital building, with 'Chinese wall' arrangements in place). The operator need not have knowledge of anatomy, as current sonographers do, with a required training period of several years. We describe first an exemplary flow of events at the site of the patient, the operator and the scan, in a case where the tissue in the target box is static. The main non-static cases are the heart (which beats constantly, but regularly) and the fetus (which moves less predictably), as discussed below. Lung movement, when regular, may be treated similarly to the heartbeat, but we prefer to make the scan fast enough to be accomplished within a breath hold. Within the spirit of the invention, the sequence may vary in minor ways evident to one skilled in the art.

Figure 11:
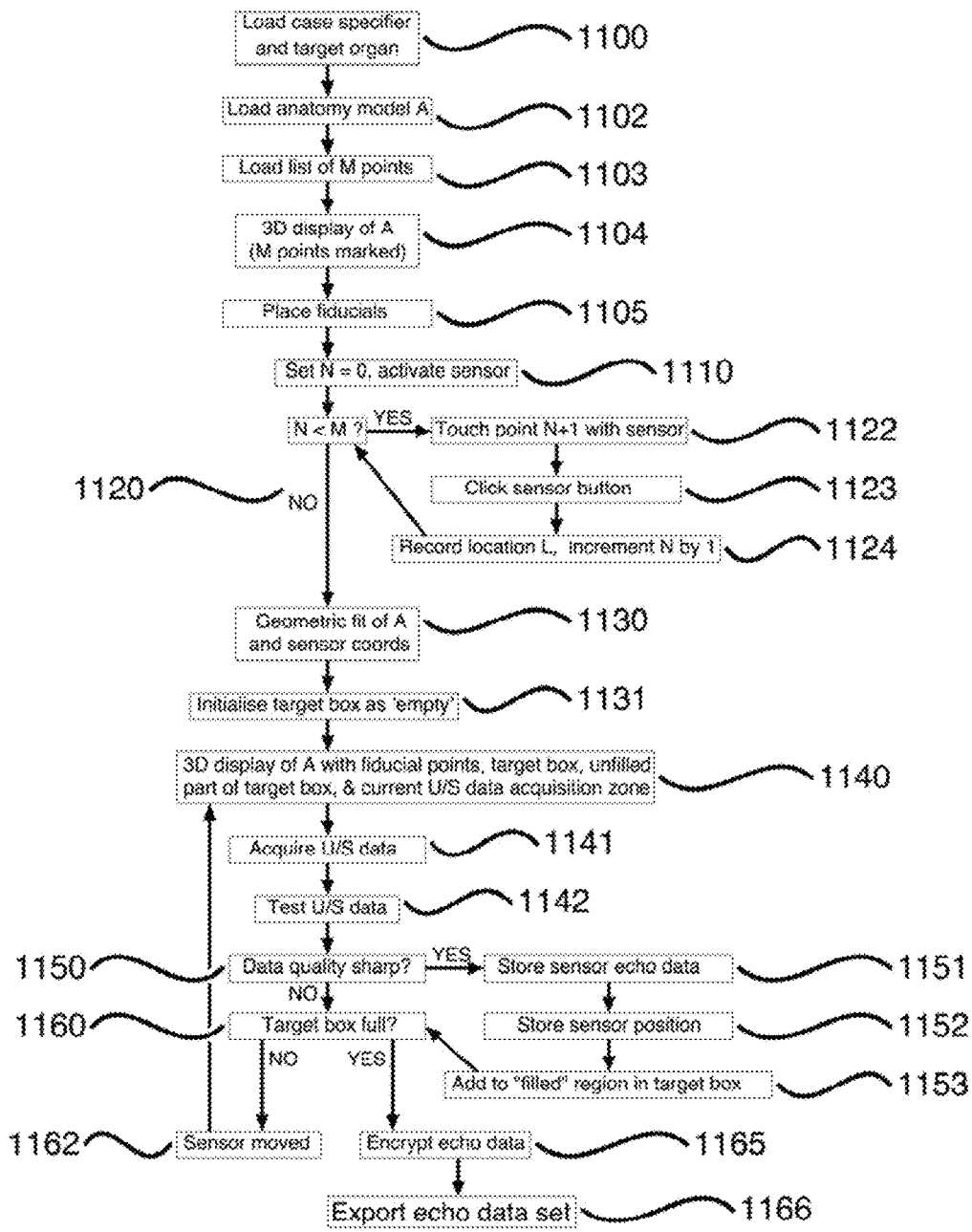
FIG. 11 shows the work flow of image acquisition according to the present invention, for a static target.

In FIG. 11, the local system 1100 first loads the identifiers of the patient (name, patient ID, etc.), as entered into by an Electronic Medical Records system (EMR), following principles well known to those skilled in the art, with a specification of the organ targeted for scan, and in some embodiments the scan type. (As described above, a Doppler scan requires data collected from widely separated points, and echocardiography with this invention requires coupling the data analysis to the phase of the patient's heartbeat. For clarity here, FIG. 11 takes the case of imaging static tissue.) The local system loads 1102 from long-term memory (local, or otherwise accessible) a simplified reference model A of human anatomy with the patient's gender and optionally such characteristics as age and body mass index (BMI). Associated with each option for a target organ is a list of a plurality of at least M=3 of fiducial points, which is loaded 1103 after the model A. In a display allowing a sufficient set of distance cues to allow human depth perception to operate, the local system displays 1104 a simple view such as a 'wire frame' surface of the anatomy model A, with the M fiducial points visually indicated. In a preferred embodiment, the first such point to be physically identified on the patient is highlighted by a brighter color, flashing, or the like.

Optionally, a view of the target organ (within the reference anatomy) is included. The next step 1105 is performed by the operator, who identifies on the physical patient the points corresponding to the displayed fiducials. This may be done mentally, by visual inspection and fixing them in the mind, but in our preferred embodiment the operator temporarily attaches physical fiducials at these points, since accuracy is more easily trained and achieved. If the position sensing function of the sensor has not been activated, this function is 1110 made active at this stage, and the number N of entered fiducials set to 0.

There follows a loop, repeatedly testing 1120 whether all fiducials have been entered. If 1120 the number N is still less than M, the operator touches 1122 the $(N+1)^{th}$ fiducial point with a standard point on the hand-held sensor, and clicks 1123 a button on the sensor or a keyboard key or otherwise signals to the system that the sensor is in position for that point. The system then 1124 records the location (by reference to the coordinate system in which the position sensor reports) as that of the $(N+1)^{th}$ fiducial, and increases N by one. (Optionally, a step not shown may test for whether the operator has become conscious of an error, and 'recall that move'.) When N has increased to M, the loop concludes. The local system then computes 1130 a best-fit transformation T between the coordinate system of the sensor's location-reporting system and the coordinates used in the reference anatomy model A. (If M=3 exactly, the best fit is an 'affine' transformation, carrying straight lines to straight lines. If M>3, the best fit may be curvilinear.)

Using the transformation T, the local system defines a polyhedral target box B in position-sensor coordinates, that can be expected to contain the target organ O, and 1131 initializes the box B as empty of echo-derived data. The local system then 1140 displays a three-dimensional view that includes the wire-frame anatomy A (transformed by • into position-sensor coordinates), optionally other visual depth cues such as a surrounding rectangular frame and a wire frame view of the expected position of the target organ O, derived from the reference model, and essentially the target box B. The local system also shows in the same three-dimensional view a polygon 550 representing the zone Z from which the sensor is currently collecting echo data, deriving the position of that zone from the sensed position of the sensor. In our preferred first embodiment the zone Z is a fan-shaped planar region, since the already-existing technology of collecting such data has been refined for this case, in order to show the derived image on a planar display. However, a curved zone Z, or a zone Z filling a three-dimensional region of space as a torch beam does, falls within the spirit of the present invention.

A loop now begins as the system acquires 1141 acquires the ultrasound echo data: the hand-held sensor emits pulses, detects the echoes as a function of time. (At this point either the echo data or the position data or both may be immediately encrypted, but in the embodiment illustrated here we show encryption as a slightly later step 1165 applied to the full scan's data.) The system's computer 1142 tests the data quality, for example by evaluating the entropy of intervals within the data, relative to the overall variation in data values. High entropy values occur where the data vary in an effectively random fashion, independent of what is echoing them: a steady level of echo from a uniform tissue, a jump between different values at a tissue boundary, or an isolated peak produced by an echo from a reflective membrane, produce lower values. A similar measure is the degree of correlation of values for particular times with the values for nearby times, as distinct from the values for times more distant. These are examples of what we shall refer to as a 'data quality measure', with a corresponding 'data quality test' of the entropy value being below a pragmatically established threshold, or the correlation being above a threshold: other such measures and tests will be evident to persons skilled in the art, within the spirit of the invention.

If the data quality test is passed, the system stores the echo 1151 and sensor 1152 position data in conjunction with the sensor's location data for that point in time. The system then 1153 uses the positional data for the acquisition zone Z to label points in the box B that are on or close to Z to as 'filled', without (in our preferred embodiment for the Indian market) completing the action of filling them with echo brightness values. In an exemplary manner of achieving this, the target box is shown as containing an open three-dimensional mesh, where nodes in 'filled' points are colored green (together with segments joining 'filled' nodes), while the others are red. Many other ways of representing this information will be evident to persons skilled in the art, within the spirit of the present invention. The system then checks 1160 whether any points in the box B remain unfilled. If some do, the system permits a small amount of time to pass, during which typically the sensor is moved 1162 by the operator (as part of a continuing smooth movement, not a shift to a new static position), and 1140 updates the display. If the box B is filled, the local system encrypts the data (unless this was already done, perhaps in parallel with the other processes in the main loop 1140-1141-1150-1160-1162-640) and exports the data set of echoes and corresponding sensor positions to the distributed system from which the local system 1100 loaded the case data, attaching identifiers that connect this data set to the current case.

We now discuss issues specific to fetal scanning. A fetus more than nine weeks after conception moves, at intervals ranging from a few seconds to several minutes, depending on gestation stage and time of day (Development of daily rhythmicity in heart rate and locomotor activity in the human fetus: Kintraia, Zarnadze, Kintraia, and Kashakashvili, J Circadian Rhythms. 2005; 3: 5). In the 'active' time this is more frequent (In 'active' hours, fetal locomotor activity augmented by 7-8 times and was equal to 91 min and 10 sec, which corresponded to 16% of the recording time, loc. cit.). After a movement, unless the fetus returns exactly to the previous position and orientation, a particular point of the fetal anatomy will create an echo from a different spatial location than before, and an echo from a particular point in space will relate to a different point of anatomy. Anatomically guided search for particular planar sections such as a section including a lengthwise cross-section of a femur is disrupted by such events, but only moderately so: usually the targeted body part has not moved or rotated far, so that a new search will not take long. However, integration into a 3D image will have problems: indeed, no single 3D image can simultaneously represent the 'before' and 'after' locations of the fetus and all its parts.

Figure 12:
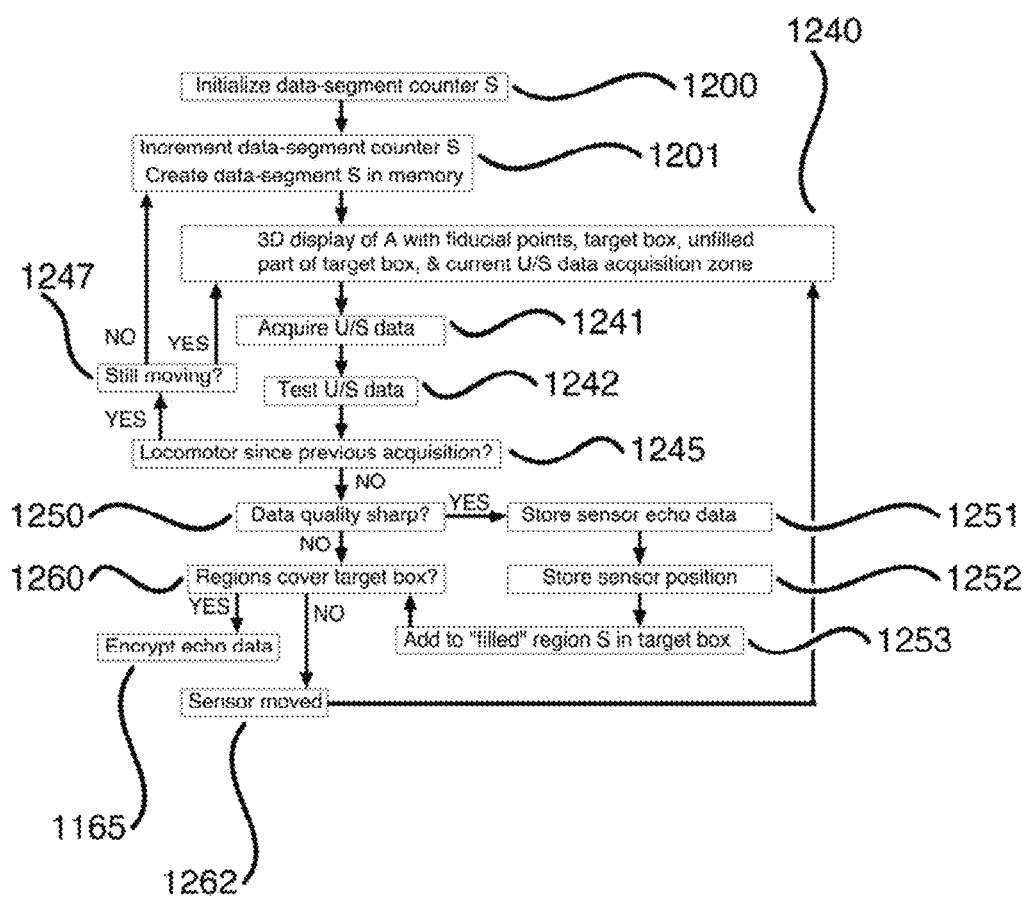
FIG. 12 shows the work flow of image acquisition according to the present invention, for an irregularly moving target such as a fetus.

The fetus does move in a coherent (though not rigid) way, so that for most clinical purposes this problem can be handled, as shown in FIG. 12. We perform the steps in FIG. 11 from 1100 to 1131, then before the display step 1240, corresponding precisely to step 1140 in FIG. 11, we initialize 1200 a segment counter S to 0 and go to the incrementation step 1201, which changes it to 1, and creates the first data segment. Proceeding from the step 1240, whether reached for the first time or in a later iteration of the loop, we acquire 1241 and test 1242 echo data, as in steps 1141 and 1142. However, we also test 1245 for fetal locomotion, optionally by the presence of motion blur inconsistent with the known motion of the sensor, or by external electrocardiography (ECG) as performed by Kintraia et al. (loc. cit.), or by other such means as are known to or discovered by those skilled in the art. If there is evidence of locomotor activity since the previous enactment of step 1241, we test 1247 whether locomotor activity is continuing. If it is continuing, we return directly to step 740, ignoring the movement-polluted data, acquire 1241 and test 1242 a new set of ultrasound data, and decide again 1245 whether locomotor activity is continuing. If locomotor activity is not continuing, we 1201 increment the counter S and create its data segment, and proceed again to 1240.

If at step 1245 there is no evidence of locomotor activity since the previous enactment of step 1241, we proceed to step 1250, corresponding precisely to step 1150 in FIG. 11. What follows corresponds to the steps after step 1150, thus 1151 and 1152 correspond now to 1251 and 1252, except that step 1153 is replaced by step 1253, adding the filled points to a record specific to the data segment numbered S. We then check 1260 whether the regions 1 to S filled so far collectively cover the target box, with margin of overlap to allow for movement. If not, we proceed to track the next (normally moved 1262) position of the hand held sensor, and repeat the display loop from the step 1240. If the regions 1 to S do cover the target box, with a pre-set allowance of overlap, we go to encryption 1165 in FIG. 11 and proceed as in that figure. The creation of 3D image data is more complex than when scanning a static structure, as we discuss below in relation to step 1450 of FIG. 14.

Motion is also significant in scanning the heart, but there it is not merely a complication, but an important object of study. With a fetus the clinician primarily needs to know about anatomy (and blood flow, with Doppler sonography), which is well revealed by a static final image. The heart, however, beats: and the analysis of that beat can be diagnostically critical. For example, the 'ejection fraction' (EF) is the volumetric fraction of blood pumped out of the left and right ventricle with each heartbeat or cardiac cycle. In the mathematics allowed by medical imaging, EF is applied to either the right ventricle, which ejects blood via the pulmonary valve into the pulmonary circulation, or the left ventricle, which ejects blood via the aortic valve into the cerebral and systemic circulation. The preferred data set is four-dimensional, with an echo density at each point in a grid labeled by (x, y, z, t), where (x, y, z) specifies a spatial location as usual, in a coordinate system where the patient is at rest, and t refers not to absolute time but to the current phase of the heart. For example, if we take as reference the 'It' peak visible in an electrocardiogram (EKG), for a heart beating regularly at 72 beats per minute, the number t refers to the time in minutes since the most recent R event, times 72. When t reaches 1, at the next R event, it resets to 0. If geometrically we collect values in a hundred gridsteps in each of the x, y and z directions, that gives one million points at which we need to estimate reflective properties from the echo data. For each ten timesteps into which we divide the period, ten million values are needed, and take longer to collect. The record to be finally produced will include estimates of values at times 0, T, 2T, etc., but these will often be interpolated from echo data acquired at intermediate times.

Figure 13:
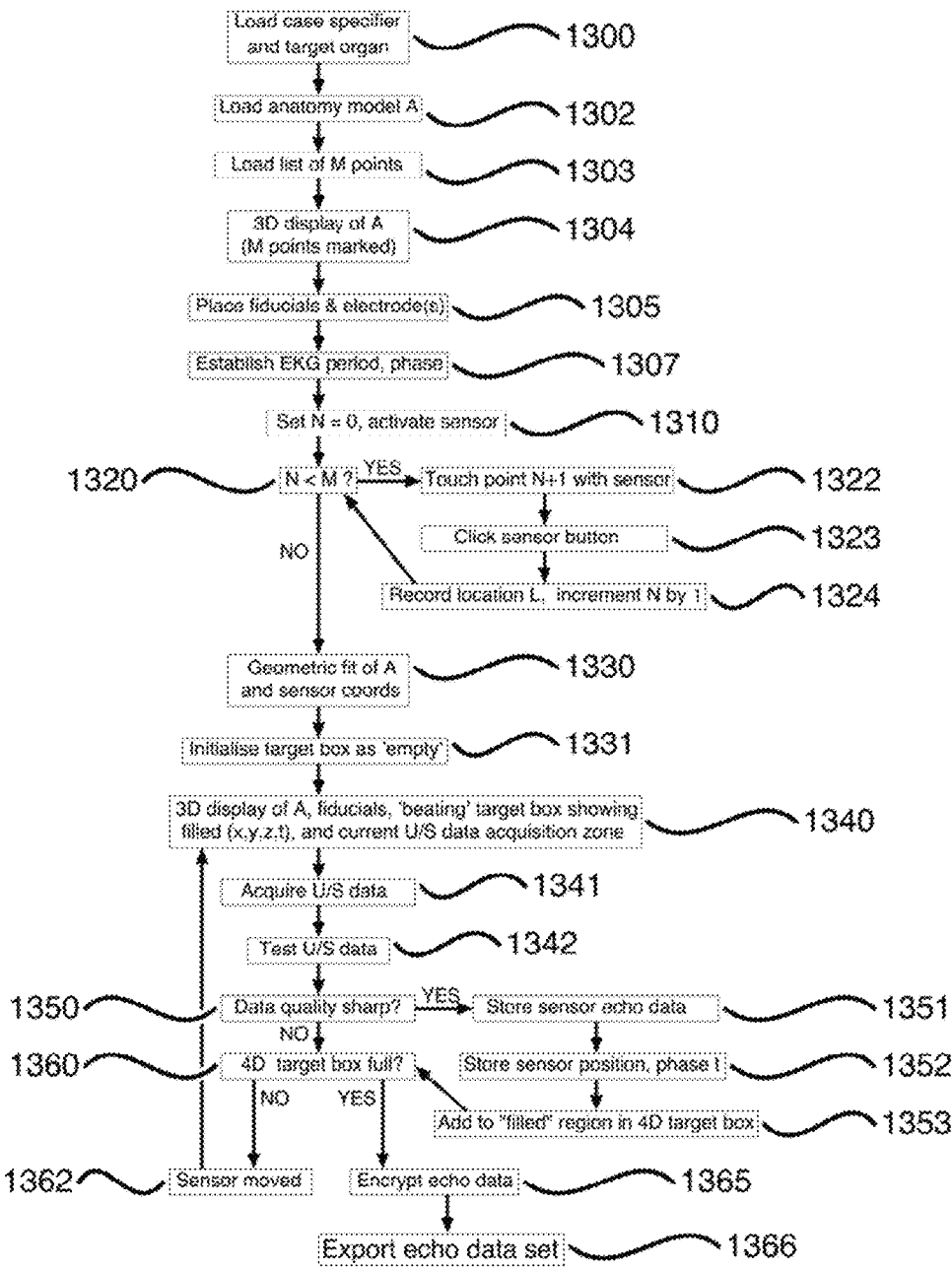
FIG. 13 shows the work flow of image acquisition according to the present invention, for an periodically moving target such as a heart.

In the static case, a small structure like the gall bladder (which would fit in an 8 cm×4 cm×4 cm box) can be sliced completely through by a typical fan-shaped acquisition zone, a sensor with 100 Hz frame rate could move its acquisition region 212 once through in a second, collecting 100 planar slices and thus a full set of data. In a sweep through the heart, the zone 212 meets different points in the heart region at different phases t (1)), and must pass through each again at other phases, from which we will interpolate data at phases 0, T, 2T, etc. FIG. 13 shows how we arrange this, in one embodiment of the present invention.

The steps 1300, 1302, 1303 and 1304 correspond exactly to the steps 1100, 1102, 1103 and 1104, with the particularities that the anatomy model A must include the surroundings of the heart in a generic patient (not the precise anatomy of the current patient), and the M fiducial points must suffice to localize it. (Points on the sternum, clavicles and scapulae are likely candidates, as are some rib points: but as some bones may be deeply covered in fatty tissue, it is desirable to allow some flexibility of choice for the operator.) In step 1305 the operator places fiducials at these M points, and also at least one electrode at a point where a good EKG signal can be received. Optionally, some or all of the fiducial objects may also serve as electrodes.

In step 1307 the system analyses the signal from the one or more electrodes, and establishes that the heart is beating regularly, in the sense that successive R-R intervals are within a preset criterion of matching in length of time and shape of the EKG signal, so that phase t can be coherently defined. (Disruptions such as cardiac arrhythmia are not compatible with the reconstruction method described below.) In an embodiment it may be useful to include a non-linear matching of successive R-R intervals, to achieve a better match oft with physiological phase than a simple ratio of times. From this point on, a phase label t can be attached to any record.

The initialization step 1310 corresponds precisely to 1110, the localization loop from 1320 to 1322 to 1323 to 1324 to 1320 is precisely that of 1120 to 1122 to 1123 to 1124 to 1120. The fitting step 1330 is again 1130, and the initialization 1331 is different only in setting up a four-dimensional box as 'empty'. However, the display 1340 differs from 1120 in that it shows not a static setting but a dynamic one, with cues as to the phase t currently displayed. In a preferred embodiment, such cues are by movement or by change of color rather than by display of numbers or a dial. In an exemplary manner of achieving this, the target box is shown as containing an open rhythmically moving three-dimensional mesh (optionally but not necessarily resembling a heart), whose motion is phase locked to the current output of the EKG, and in which a node is colored green when at the current phase the point it is in is 'filled', and otherwise colored red. Thus for example if the operator first controls the sensor to move the acquisition region 812 once downward through the heart, giving echo data corresponding to successively lower planes in the physical space of the heart, the display then shows a wave of green points moving down the mesh, which remains mostly red. An efficient strategy for the operator is then to sweep downward again at the same speed, but with a different phase, such as keeping the acquisition region 812 just above the green wave, or at some chosen height above it. Some practice in a virtual training system will provide the operator with the necessary skill to completely eliminate red points, in a minimal number of sweeps. Many other ways of representing information as to 'filled' and 'un-filled' points (x, y, z, t) will be evident to persons skilled in the art, within the spirit of the present invention. This technique extends straightforwardly to Doppler imaging (with three times the number of sweeps, from three substantially different sensor locations), with the merit that blood flow data in a cardiac artery are acquired for a full cycle, without the operator having to track the artery by moving the sensor to keep the artery in the acquisition zone 812. Furthermore, since a three-component Doppler acquisition gives information about blood flow in every direction, in the final four-dimensional data set the flow along such an artery can be followed along the whole length of that artery, not merely when it is toward or away from the sensor.

With the display 1340 as described above, the remainder of the logical flow is identical to that of FIG. 11, replacing each initial '11' in a label by '13', save that step 1352 stores the current phase t as well as the current sensor location and orientation, step 1353 adds to the 'filled' region of a four-dimensional box instead of to the three-dimensional data structure of step 1152, and step 1360 checks for the existence of unfilled parts of that four-dimensional box. The successive sweeps described above make it clear that the operator must make more sweeps, but this does not modify the flow organization of the acquisition system.

Figure 14:
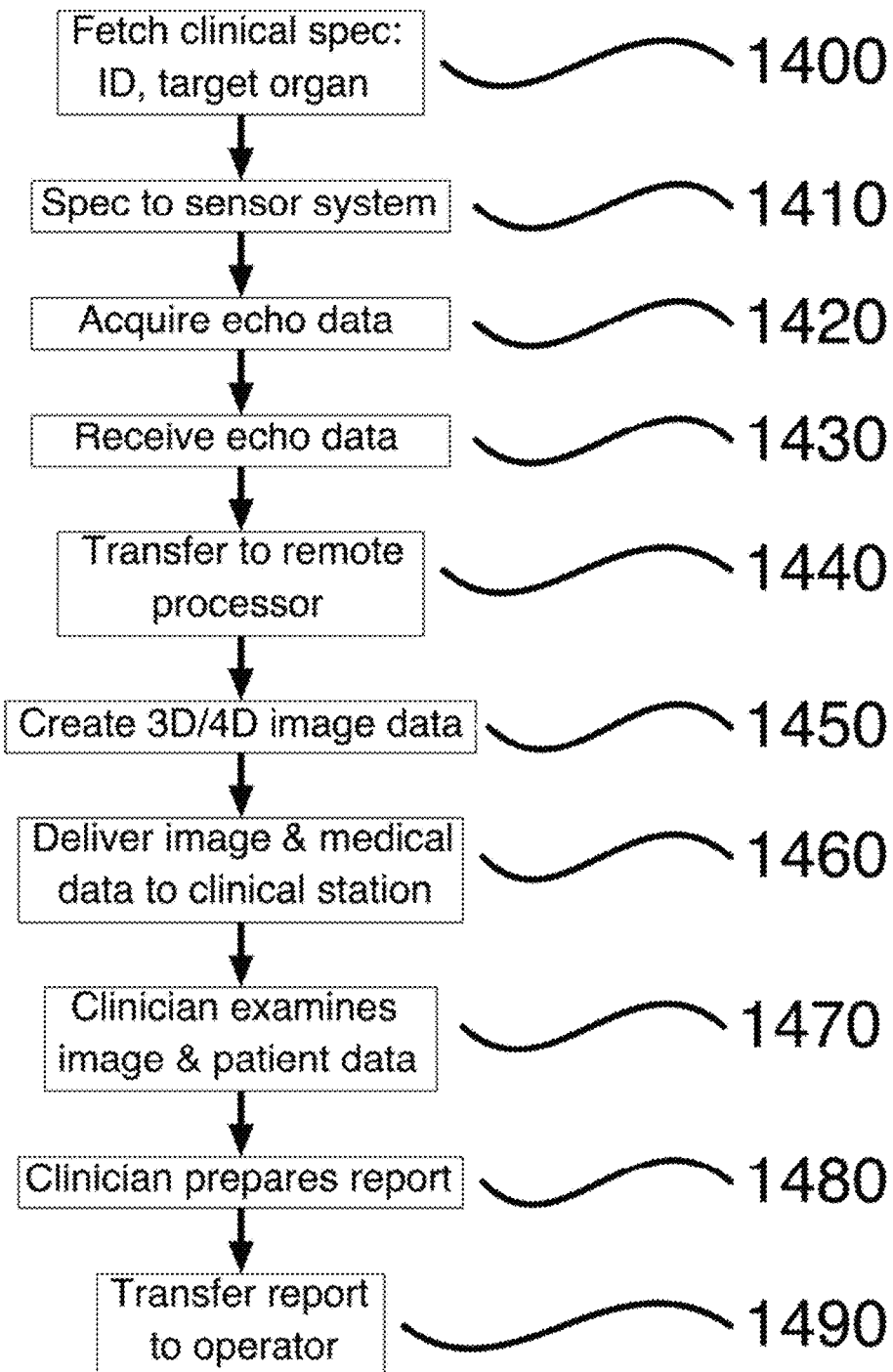
FIG. 14 shows the overall work flow of acquiring, using and reporting of ultrasound imagery, according to the present invention.

FIG. 14 shows how the local flow within an example of FIGS. 11, 12 or 13 is embedded in the distributed system. First, the clinical requirements are acquired 1400 from a local EMR, or by local entry from a registered user who is registered with the system as entitled to enter such data and requests. (As an example, this might be a nurse at a one-doctor clinic, or the doctor in person. Such small clinical operations are of particular interest for the present invention, as they may not be licensed for ultrasound use by a government seeking to prevent sex determination, or may lack access to a sonographer trained with the anatomical skills required in using current equipment, particularly at low cost.) The resulting data are passed 1410 to the local system managing the sensor, which 1100 receives them and 1420 performs (with the human operator) the steps in FIGS. 11, 12 or 13, which 1166, 1266 or 1366 return echo data, including the associated positions of the sensor. These are received 1430 by the distributed system, and transferred 1440 to a processor with large computational power that performs the numerically intensive step 1450 of creating a three-dimensional image, for the static and fetal cases, or a four-dimensional image, for the cardiac case. The latter is straightforward (though computationally intensive), since each echo record in a particular direction from a sensor in a particular location at a particular moment implies reflectivity intensity values at that time (plus the sound travel time) at each point along the line in that direction from that position. The fetal case is more complicated, since we have a number of 'between locomotion' segments to deal with. In one embodiment the system first chooses the largest such filled region as a reference, then finds for the second largest the translation and rotation that achieves the best matching of reflectivity values where it overlaps with the first, discarding values that correspond to the wall or exterior of the womb. If there are more than two segments the system then finds for the third largest the translation and rotation that achieves the best matching of reflectivity values in the subset where it overlaps with the first and the moved second, iterating until all segments have been included in a fused three-dimensional layout. This is not sufficient in general, however, since often an overlap will correspond to a part of the fetus that has changed non-rigidly, by bending at one or more joints, between the data-segments involved. The system therefore fits a generic numerical model of a fetal skeleton (preferably matched to gestational age) to the most bone-like reflections in the fused layout, to identify which bone is which. With this information, and data on the angles through which each joint can move, the system defines a mapping of the bones within the second segment to those of the first, and extends this to the soft tissues to give a non-linear correspondence from one to the other that permits a fusion of the two three-dimensional partial images. (The art of such fusion of non-linearly related images is well established, as is illustrated in 3D by 'Image registration system and method', US 20080095465 A1 to Mullick, Poston and Nagaraj, and many other publications. In various contexts it is also known as montage, stitching and mosaic. Any means of achieving such a fusion of partial images may be used within the spirit of the present invention.) If there is a third data segment, the system similarly fuses the corresponding partial image with the fusion of the first two, and so on until all data segments have been used.

The choice of performing image creation at the stage 1450 is suggested by the 'cloud' computing model, where a powerful processor does not sit idle when (for example) a sensor system to which the processor is bound is not performing a scan, and by the security advantage of the local non-existence of images. This choice is thus our currently preferred embodiment of the invention, though the raw echo data are a larger dataset than the 3D or 4D image created from them. Limited bandwidth or high data transfer costs can thus alter the preferred solution, though the problem is mitigated by the fact that the data need not be transferred in real time (as they would if, for example, a remote operator were to guide the sensor by controlling a local robot). Near-real-time response, aiming at a final clinician's report in minutes rather than a response in milliseconds, is less dependent on high and uninterrupted bandwidth.

The created three-dimensional or four-dimensional image, with the clinical record and patient ID (which optionally may exclude the patient's real name or the scanning location, for security reasons) is delivered 1460 to a station where a clinician has indicated availability for immediate study and report. (The word 'station' here includes any system, from desktop to tablet or future-generation smart phone, that is capable of receiving the data and supporting the necessary examination.) In a preferred embodiment the distributed system has access to a number of clinicians and can seek an available one, greatly reducing the scheduling problems and random-arrival queue clusters that are inevitable with a single clinician, or a fixed allocation of particular clinicians to particular scanning sites.

The clinician studies 1470 the three-dimensional or four-dimensional image with tools well known to those skilled in the art, such as making all but bone (or another tissue type) transparent, rotating the view, showing a slice at an arbitrary angle (unrelated to the orientation of the acquisition zone Z in any step 1141), quantifying distances or volumes, etc. Automated or semi-automated tools of kinds well known to the art, or additional innovations, may assist by quantifying distances such as femur length, volumes (including derived quantities such as ejection fraction in the case of echocardiology), count and size of gallstones or kidney stones, straightness and stage of healing for a broken bone, etc., as appropriate in the medical context. The clinician then prepares 1480 a report on the status of the patient, using the clinical record and the image data. In a preferred embodiment this report becomes part of a secure permanent record, so that any information revealed remains subject to audit for clinical or regulatory purposes. Two-dimensional or three-dimensional images may be included in the report, in accordance with clinical utility and regulatory constraints. The distributed system then passes 1490 the report to the local operator, directly to the local clinician who requested the scan, or to the local electronic medical records system to be called up by any authorized person (in which case our preferred embodiment notifies the report's arrival to those flagged as concerned with the particular case).

It is important to distinguish here the various kinds of data that are integrated in the present invention. We will refer to the following:

Pre-image data, which includes energy emitted by or reflected from the tissue to be studied, such as light emitted by fluorescence, or reflections sound or electromagnetic radiation originating at the sensor, and further includes measured values of such data, whether as an analog signal within the sensor such as a voltage level, or as a digitized version of the signal values, and further may include data concerning the emitted signal, and reduced forms of such data. In the example displayed in FIG. 7, pre-image data include the transmission timing data 721 of emitted pulses 707, the echoed sound 708, the values of the analog signal 715 of the sensed echoed sound, the converted digital signals 725 of these values, and the data flow 735 specific to particular emitted pulses 707 identified by the comparison by the echo identifier 730, optionally including Doppler comparison of the echo's frequency with that of the emitted signal. Similarly, in frequency domain optical coherence tomography (FD-OCT), pre-image data include the reference beam travelling uninterrupted from an emitter, the beam reflected from tissue, the interference signal created by physically superposing these, the analog values created by sensing this interference signal, their digitization and its Fourier transform, and the identification of values corresponding to particular phase differences of the two beams, and thus to differences in time of travel.

The term 'pre-image data' includes time series of such data, and the timing data that make it possible to integrate synchronous data of different types. Though many examples discussed in the present disclosure are specific to reflected ultrasound, nothing herein is to be construed as a restriction to that case.

Sensor-frame image data, constructed as in 740 from the pre-image data by integrating transmission timing data 721 with the echo data flow 735, to give reflection intensity values along particular rays and thus (typically) pixel values in a rectangular array that can be displayed in a planar image 106. These planar pixel values may exist, but are not required to exist, in an embodiment of the present invention.

Base-frame sensor position data, including but not limited to (in various embodiments) analog values of electromagnetic wave data, accelerometer data, images taken of or from the sensor, and ultrasound signals, their digitization, and specifications derived from such data of the location and orientation of the sensor relative to a fixed base, which may be a signal emitter, a camera, a cradle which holds the sensor in a reference position, and other such bases as are well known to those skilled in the art.

Fiducial position data, specifying the coordinates of the fiducial objects in the base-frame coordinate system. These may be obtained by their inclusion within the position-sensing system (for example, a Polhemus 'Flock of Birds' can report the positions of multiple objects relative to the same base, if each contains a unit of the system), or by touching them with the tracked image sensor. Optionally, one might sense their locations using a separate subsystem, and transform the resulting coordinates into a frame in which the image sensor's position is also known, but our preferred embodiment gives them in a common coordinate frame directly.

Patient-frame sensor position data, specifying the instantaneous position of the sensor in a frame of reference in which the fiducials have standardized locations, subject to anatomical variation. For example, if for upper-body examination fiducials are placed on the acromial extremities of a patient's clavicles, at a distance D apart, a patient-oriented coordinate system would typically require their locations to have the coordinates ($\pm$D/2, Y, Z) with shared values of Y and Z. Similarly, it might require a fiducial on the easily-located sixth vertebra to have the location (0, 0, 0). These requirements would fix the patient-frame coordinates of all other points. (Other such schemes, some more complex, will be evident to persons skilled in the art.) For the base-frame fiducial position data to have this form would constrain the placement and orientation of the base: to avoid this we prefer to position the base freely, and determine from the sensed base-frame locations of the fiducials, at anatomically specified positions, the affine transformation between base-frame coordinates in general and the corresponding patient-frame coordinates.

Note that since this transformation depends on parameters such as D, the expected region of interest 505 occupied by a target tissue cannot be given as (for example) a polyhedron with a fixed set of coordinates for its corners. For instance, in a typical adult the apex of the heart lies 8 cm to 9 cm from the mid-sternal line, but in an infant both D and this distance are smaller. The computation of the target region of interest 505 in patient frame coordinates is thus a substantial step of the invention, requiring application of both mathematical and anatomical knowledge: however, with the task once specified, the details of the algorithm can be developed by any person or group sufficiently skilled in the mathematical and anatomical arts.

In the terminology used here, this 'target region of interest' 505, with respect to which data are to be acquired, is distinct from the 'acquisition region' 550 with respect to which at a specific moment the sensor is acquiring data.

Patient-frame image data, giving pixel values in a three-dimensional array specified with reference to the frame of reference in which the fiducials have their required values.

These data may be assembled from sensor-frame image data, as created 740 in FIG. 7, or directly from pre-image data and sensor position data as defined above.

Display-frame sensor data, derived from the base-frame sensor position data, which determine where in the display exemplified in FIG. 5 the acquisition region 550, in terms of the graphical coordinate system used in the display. (Typically, these coordinates specify lateral and vertical position relative to the screen, and 'depth' or distance from the viewer.) In our preferred embodiment the transformation from base frame to display frame arranges that displayed movements appear to the user to be parallel to the sensor movements that the user directly wills, sees and feels: the determination of this transformation can be done once for all, in calibration of the system, if the base and display are physically fixed in a particular geometric relationship.

These distinctions are important both for the effective design of an embodiment of the present invention, and for the aspect of image security. Until the stage at which sensor-frame or patient image data exist, there exists nothing that can be transferred to a display and interpreted by a human as information about a fetus, a heart, or a malignant growth. Intercepting the pre-image data alone does not suffice for imaging: it must be integrated with at least the information of the transmission timing data 721 for a planar image, or additionally with sensor position data 719 for a 3D image (unless a more costly 3D sensor is used), before any breach of anatomical security can occur. Creating an interception system capable of performing such integration would involve a similar effort to the creation of an entirely independent imaging system, and its sale and use would be restricted by the same Indian laws that already govern local-display ultrasound system.

This is in great contrast to such imaging devices as an indirect ophthalmoscope, which illuminates the inner eye, collects light and physically forms an image, which may immediately be viewed by the clinician or captured by a still or video camera. The level of processing required before in any sense an image exists provides a multiplicity of options for security, which will be evident to those skilled in the art, by encryption or physical inaccessibility at any point in the pre-image information flow. Encryption or inaccessibility even of low-bandwidth parts of the pre-image data, such as the timing or positional data, is sufficient to block unauthorized image creation.

A computer is a programmable machine, It. need not be a single programmable component, hut may be multiple programmable components in communication with each other as a unit still defined as a computer. Tins means that the computer can execute a program, code or programmed list of instructions/commands and respond to new instructions that it is given When referring to a desktop model, the term "computer" technically only refers to the computer itself not the monitor, keyboard, mouse and other ancillary addenda. Still, it is acceptable to refer to everything together as the computer. Some of the major parts of a personal computer (or PC) include the motherboard, CPU, memory (or RAM), flash drive, EPROM, hard drive, audio card, speakers, display and video card or graphics processing unit (GPU). In the present disclosure, "the computer" refers to all such components, including processors that may be located in the hand-held sensor itself (in particular, though not exclusively, to perform local encryption), as well as those in the larger system that manage display, distant communication, and the other functions common to current lap-top and desktop systems. While personal computers are by far the most common type of computers today, there are several other types of computers, and we do not intend the term to refer to only one type.

A general apparatus useful in practices of the present technology includes:

an on-site non-invasive scanning device for producing image data relating to an internal target volume of a subject;

a computer configured to receive the image data from the non-invasive imaging device and execute code to track motion of the non-invasive scanning device (e.g., by executing code, processing data, analyzing data, constructing useful information as text or image, etc.);

a display screen in communication with the computer configured to receive image data (or information in any useful form) from the computer and provide image (including text) feedback to an operator of the non-invasive imaging device that comprises information associated with a display of motion and imaged content through a three-dimensional virtual model of an image-acquisition region of the non-invasive scanning device through a three-dimensional virtual model of the internal target volume. The computer is configured to acquire data from the non-invasive imaging device as the operator moves the non-invasive scanning device, and there is an information transmission link for transmitting the acquired data to at least one computer system that is not on-site. The at least one computer system that is not on-site (this may still be a relatively local computer, in the same town, village, city or country as the on-site non-invasive imaging system) being a geographically and physically separated computer system configured to receive, process and analyze the transmitted data; and the at least one geographically separated computer system providing processed and/or analyzed data to an on-site recipient computer.

A desirable feature of the data transformations above, for the purposes of the present invention, is that they occur in 'real time', which we may define variously for different subsystems (instantaneity being physically impossible). For position data we define it here as involving a delay of no more than 100 milliseconds between the moment that the sensor is at a particular position, and the moment when the corresponding representation 550 of the acquisition zone appears to the user. (A preferred embodiment would limit the delay to around 20 milliseconds, so that the display is at most one image-refresh behind the actual position.) Anatomically guided ultrasonography requires a similar limit on the delay, so that the planar image 106 follows the changes in sensor position without perceptible delay, which would make the user's task more difficult and slow. The present invention can be slightly more relaxed in this respect, since the image data are not displayed to the user: however, where we display derived image data (such as bone locations, or the modifications illustrated in FIGS. 9 and 10), the additional processing makes the overall condition of 'no perceptible delay' more stringent. Even where we do not display image-derived data, we provide feedback about data quality, which the user should be able to correct within seconds.

We therefore desire that each of the steps in the above processing from pre-image data to image data, as well as from base-frame sensor position data to displayed positions of the acquisition region, determination of displayable regions where further acquisition is needed, and optional extraction of image features such as bones. Many of these steps could be performed by a human or a team of humans, manipulating symbols on paper. A skilled algebraist, given the list of sensed fiducial positions and the corresponding anatomical locations with their adjustable coordinates, could extract in less than an hour the coefficients of the affine transformation A between base-frame sensor position data and patient-frame sensor position data, and apply A to transform in under a minute a new set of (x, y, z) and (roll, pitch, yaw) base-frame data into patient-frame data. However, this would be of no value for the present invention. Although the mathematical procedures involved predate digital computers, they combine with a computer to something new, an embedded algorithm producing results in real time. In some cases the algorithms used here are known to those skilled in the art: in particular, the display of a virtual object moving in synchrony with a real object is in wide use, from the 2D cursor moving with a mouse to 3D objects in video games. We do not claim novelty for all the real-time embedded algorithms used within all steps of the present invention, but in no case do they perform on a computer what was previously done for the same purpose without one. The real-time speed permitted by a computer allows their assembly into a system which could not be embodied without one, so that their novelty must be assessed relative to other computer-based procedures: corresponding manual procedures, achieving the same real-time result, simply do not exist. An embedded algorithm may consist of a set of specialized fixed connections between logical elements of a computer chip such as a digital signal processor (DSP) or an application-specific integrated circuit (ASIC), as code stored in memory that instructs the operating system of a computer to perform specific logical and numerical steps, or hybrid elements such as a field-programmable gate array (FPGA). All of these fall within the meaning used here of 'real-time embedded algorithm', which we define as 'exercised' when the computer or component performs the steps required.

Although specific examples of components, apparatus, materials, frequencies and times are provided, one skilled in the art is aware that variations from those specific examples may be used in the practice of the generic invention described and enabled herein.

What is claimed:

1. A method of acquiring ultrasonic data, the method comprising:
   (i) providing an image-acquiring system, the system comprising: a first computer, a non-invasive imaging device comprising an ultrasound probe, a sensing system comprising location and/or orientation sensors, and a visual display;
   (ii) selecting a three-dimensional target region via an input operation to the first computer, the selecting performed by a local user, wherein the target region represents a region within a physical body of a subject;
   (iii) the computer calculating, in response to the selecting, a plurality of fiducial positions corresponding to anatomical features in the target region;
   (iv) prior to acquiring the ultrasonic data, the computer creating a model of the target region comprising a plurality of target locations representing a plurality of planned locations in the target region at which ultrasonic data is to be acquired, and displaying a visual representation of the model comprising a plurality of graphical elements, each graphical element representing a corresponding one of the plurality of target locations;
   (v) acquiring the ultrasonic data at each of the planned locations with the ultrasound probe of the non-invasive imaging device, the ultrasound probe operated by the local user, calculating a three-dimensional acquisition position for each piece of the acquired ultrasonic data, the acquisition position determined based on information from the sensing system and the fiducial positions, and associating the acquisition position with a corresponding one of the target locations and a corresponding one of the graphical elements;
   (vi) executing, with the computer a transformation of the visual representation comprising:
      a) performing a data quality test at each target location, wherein the data quality test is based on a predetermined criteria of quality;
      b) for any target location that fails the data quality test, altering the graphical element corresponding to the failed target location to indicate failure of the data quality test at that location; and
      c) displaying the transformed visual representation comprising the updated graphical elements on the visual display.

2. The method of claim 1, where the ultrasonic data comprises anatomical image information for the target region.

3. The method of claim 2, where the anatomical image information is transmitted to a second computer, wherein the second computer is connected to the first computer via a network, and wherein an anatomical image of the target area is generated from the ultrasonic data by the second computer.

4. The method of claim 2, wherein the non-invasive imaging device further comprises encryption hardware, and wherein the encryption hardware is configured to restrict access to the anatomical image information.

5. The method of claim 1, further comprising:
   tracking motion of the ultrasound probe during the acquisition of the ultrasonic data;
   determining, with the first computer, motion parameters based on the tracked motion of the ultrasound probe;
   comparing the motion parameters to a set of stored parameters which are stored in a memory of the first computer, and displaying a result of the comparing on the visual display.

6. The method of claim 1 wherein the data quality test comprises:
   analyzing, with the computer, each target location to determine if acquired ultrasonic data is associated with the target location; and
   if no acquired ultrasonic data is associated with the target location, determining that a gap exists.

7. The method of claim 1, wherein the first computer causes the visual display to display a geometrically accurate representation of the target region, including a representation of the fiducial positions, comprising correct aspect ratios of three dimensions of the target region and correct registration of the displayed fiducial positions with respect to the target region.

8. The method of claim 1, wherein the non-invasive imaging device is configured to detect a component of velocity of flow of matter within the target region, the component of velocity being in directions away from or towards the ultrasound probe.

9. The method of claim 1, where the local user acquires the ultrasonic data from multiple ultrasound probe positions of at least three substantially different perspectives relative to the target region.

10. The method of claim 1, further comprising performing motion artifact correction on the acquired ultrasonic data.

11. The method of claim 1, wherein the acquired ultrasonic data represents a time series, and wherein the ultrasonic data is acquired in synchrony with a measure of cardiac phase, and a four-dimensional ultrasound image comprising a series of 3-dimensional ultrasound images of a time cycle of heart motion is constructed from the ultrasonic data and the measurement of cardiac phase.

12. The method of claim 1, further comprising generating, with the second computer, an ultrasound image from the acquired ultrasonic data, and preparing a report based on the ultrasound image.

13. The method of claim 1, further comprising generating, with the second computer, an ultrasound image from the acquired ultrasonic data, and preparing a plan of treatment based on the ultrasound image.

14. The method of claim 1, where the non-invasive imaging device detects, with the ultrasound probe, a component of velocity of flow of matter within an internal volume of the subject, the component of velocity being in directions across the direction of view of the ultrasound probe.

15. The method of claim 1, where ultrasound information generated by the second computer from the ultrasonic data is displayed in association with the transformed visual representation on the visual display.

16. The method of claim 1, wherein ultrasound information generated by the second computer from the ultrasonic data is not displayed in association with the transformed visual representation on the visual display.

17. The method of claim 1, where the graphical elements comprise dots.

18. The method of claim 1, where the target region comprises target tissue and/or a target organ.

19. The method of claim 1, where the visual representation comprises a geometric representation of a body.

20. The method of claim 1, wherein the predetermined criteria of quality is numerical.

\* \* \* \* \*